United States Patent
Haider et al.

(10) Patent No.: US 11,998,393 B2
(45) Date of Patent: Jun. 4, 2024

(54) SYSTEM AND METHOD OF SIGNAL PROCESSING FOR ULTRASOUND ARRAYS WITH MECHANICALLY ADJUSTABLE TRANSDUCER SHAPES

(71) Applicant: GE Precision Healthcare LLC, Wauwatosa, WI (US)

(72) Inventors: Bruno H. Haider, Rehoboth Beach, DE (US); Kjell Kristoffersen, Oslo (NO); Edouard DaCruz, De Cimiez-Bat (FR); Flavien Daloz, Biot (FR); Geir Ultveit Haugen, Stabekk (NO); Johan Kirkhorn, Horten (NO); Anders R. Sørnes, Oslo (NO)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 17/075,103

(22) Filed: Oct. 20, 2020

(65) Prior Publication Data
US 2022/0117584 A1   Apr. 21, 2022

(51) Int. Cl.
*A61B 8/08* (2006.01)
*A61B 8/00* (2006.01)

(52) U.S. Cl.
CPC .......... *A61B 8/5207* (2013.01); *A61B 8/0883* (2013.01); *A61B 8/4494* (2013.01); *A61B 8/461* (2013.01)

(58) Field of Classification Search
CPC ... A61B 8/5207; A61B 8/0883; A61B 8/4494; A61B 8/461; A61B 8/445; A61B 8/12;
(Continued)

(56) References Cited

U.S. PATENT DOCUMENTS

| 5,388,461 A | 2/1995 | Rigby |
| 5,474,070 A | 12/1995 | Ophir |

(Continued)

FOREIGN PATENT DOCUMENTS

JP      5709366 B2      4/2015

OTHER PUBLICATIONS

Behar V. Techniques for phase correction in coherent ultrasound imaging systems. Ultrasonics. Aug. 2002;39(9):603-10. doi: 10.1016/s0041-624x(02)00376-1. PMID: 12206626. (Year: 2002).*

(Continued)

*Primary Examiner* — Patrick Fernandes
*Assistant Examiner* — Nicholas A Robinson
(74) *Attorney, Agent, or Firm* — Boyle Fredrickson S.C.

(57) ABSTRACT

A deployable ultrasound imaging device is operably connected to an ultrasound imaging system including a processing unit configured to operate the transducer and the individual segments in order to emit ultrasound signals from the segments and to receive ultrasound signals from the structures surrounding the segments. The ultrasound imaging system/processing unit can process the transmitted and received signals by beamforming to direct the ultrasound signals emitted from the segments in order to provide data for an ultrasound image of the desired structure(s). The ultrasound imaging system/processing unit mechanically or acoustically determines the position of the individual segments with regard to one another to determine the angular position of the segments with regard to one another. Using the angular position, the ultrasound imaging system/processing unit can apply a beamforming correction to the ultrasound signals emitted from and/or received by the segments in order to produce an accurate ultrasound image.

5 Claims, 15 Drawing Sheets

(58) Field of Classification Search
CPC ....... A61B 8/4272; A61B 8/4483; A61B 8/56; A61B 8/4488
See application file for complete search history.

(56) References Cited

U.S. PATENT DOCUMENTS

| | | | |
|---|---|---|---|
| 5,735,282 | A | 4/1998 | Hossack |
| 5,910,115 | A | 6/1999 | Rigby |
| 6,071,240 | A | 6/2000 | Hall et al. |
| 6,392,330 | B1* | 5/2002 | Zloter .................. B06B 1/0655 310/366 |
| 6,506,160 | B1 | 1/2003 | Van Stralen et al. |
| 7,220,233 | B2 | 5/2007 | Nita |
| 7,367,945 | B2 | 5/2008 | Dasgupta et al. |
| 7,500,954 | B2 | 3/2009 | Wilser |
| 7,615,009 | B2 | 11/2009 | Koste et al. |
| 7,740,583 | B2 | 6/2010 | Rigby et al. |
| 7,775,982 | B2 | 8/2010 | Hazard et al. |
| 9,072,495 | B2 | 7/2015 | Specht |
| 9,220,478 | B2 | 12/2015 | Smith et al. |
| 10,405,830 | B2 | 9/2019 | Garbini |
| 2006/0276711 | A1* | 12/2006 | Yuan .................. A61B 8/445 600/437 |
| 2008/0146937 | A1 | 6/2008 | Lee |
| 2008/0287798 | A1 | 11/2008 | Lee |
| 2014/0058266 | A1 | 2/2014 | Call |
| 2018/0098753 | A1 | 4/2018 | Haider |
| 2018/0279998 | A1 | 10/2018 | Specht et al. |
| 2021/0272339 | A1* | 9/2021 | Kim .................. A61B 8/5207 |

OTHER PUBLICATIONS

A comparative evaluation of several algorithms for phase aberration correction IEEE Trans. Ultrason. Ferro. Freq. Contr., 41 (1994), pp. 631-642 (Year: 1994).*

Estimation of subsample time delay differences in narrowband ultrasonic echoes using the Hilbert transform correlation, in IEEE Transactions on Ultrasonics, Ferroelectrics, and Frequency Control, vol. 41, No. 5, pp. 588-595, Sep. 1994, doi: 10.1109/58.308493., (Year: 1994).*

Trahey, G. et al., "Experimental results with a real-time adaptive ultrasonic imaging system for viewing through distorting media", IEEE Transactions on Ultrasonics, Ferroelectrics, and Frequency Control, vol. 37, No. 5, pp. 418-427, Sep. 1990, doi: 10.1109/58.105248.

Peralta et al., "Coherent Multi-Transducer Ultrasound Imaging", IEEE Tmsactions on Ultrasonics, Ferroelectrics, and Frequency Controls, May 2019, di: 10.1109/TUFFC.2019.2921.103.

Peralta et al., "Coherent Multi-Transducer Ultrasound Imaging," IEEE Transactions on Ultrasonics, Ferroelectrics, and Frequency Control, May 2019, 16 pages.

CN application 202111224016.7 filed Oct. 20, 2021—Office Action dated Sep. 9, 2023; 16 pages.

* cited by examiner

Transmit / receive pulse time-of flight measurement

SYSTEM AND METHOD OF SIGNAL PROCESSING FOR ULTRASOUND ARRAYS WITH MECHANICALLY ADJUSTABLE TRANSDUCER SHAPES

FIELD OF THE DISCLOSURE

The present disclosure relates generally to ultrasound devices, and more particularly to systems and methods for signal correction when utilizing ultrasound devices including moveable signal generating and/or receiving segments.

BACKGROUND OF THE DISCLOSURE

Ultrasound imaging devices may be used to obtain information about objects, such as tissues, organs, and other anatomical regions of a patient, that may be difficult to gather via external scanning or imaging techniques. The ultrasound device can be formed as an invasive device that can be inserted within the object in order to obtain the information about the interior structures of the object. In the situation where the object is patient, the ultrasound device can be formed as a deployable catheter which may be inserted intravenously into a patient's body. In one example, the device may be used for intracardiac echocardiography imaging where the device is introduced into the heart via, for example, the aorta, inferior vena cava, or jugular vein. In many configurations, the ultrasound devices include an ultrasound probe with an aperture size conforming to dimensions that enable the devices to fit through an artery or vein. Thus, on many occasions the resolution and penetration of the ultrasound probe is limited by a maximum allowable diameter of the invasive device.

Recently, improved ultrasound devices have been developed to overcome the limitations on resolution and penetration due to the size of the aperture in which the device is inserted. Specifically, as disclosed in U.S. Non-Provisional patent application Ser. No. 15/930,302, filed May 12, 2020, entitled Methods And Systems For An Invasive Deployable Device, the entirety of which is expressly incorporated herein by reference for all purposes, an ultrasound device has been formed which includes at least a pair of ultrasound signal emitting/receiving segments that are moveably connected to one another. Thus, the segments forming the device in their collapsed form can be inserted through a smaller opening than it would be possible if the segments were expanded. Once inserted, the segments can be expanded when the device is positioned where desired. The movement of the segments relative to one another increases the imaging aperture and thereby increases the resolution and penetration that can be achieved using the ultrasound device formed of the moveable segments compared to prior art single segment ultrasound devices.

However, one issue arising from the use of the ultrasound devices including the moveable segments is the signal correction required to compensate for any misalignment of the segments with regard to one another in the expanded form. More specifically, when the segments are displaced form the collapsed form into the expanded form at the desired location, for a variety of reasons the segments may be positioned at an angle with regard to one another that is different from the desired angle, for example, not in a single planar configuration. In this angled configuration, when the ultrasound signals are emitted from and/or received by each segment to provide the data forming the ultrasound images, the angle creates errors in the signal processing due to the incorrect assumptions utilized concerning the relation of the positions of the segments relative to one another. Further, the segments themselves are structurally not as sturdy as in a conventional transducer. This can cause the shape of the segment to become distorted, e.g., instead of being on a flat plane, it may be twisted. As a result of these modifications to the positioning of the segments relative to one another and/or the position of the individual transducer elements on a distorted segment structure, the beamforming or image formation utilizing ultrasound signals from these transducers must take these effects into consideration.

Also, these transducers including the moveable segments have a number of individual transducer elements on the transducer segments that collectively form a number 2-5 times more than on conventional static ultrasound transducers. As the number of available beamforming channels for transmission of the signals to/from the transducer elements is already limited in prior art ultrasound imaging devices/catheters due to the inner diameter of the cable or catheter lumen, the increase in transducer elements in the expandable ultrasound imaging devices/catheters greatly increases the significance of this problem.

Therefore, it is desirable to develop a system and method for the processing of ultrasound signals emitted from and received by moveable segments of an ultrasound imaging device that can determine the relative position of the segments with regard to one another and provide an necessary correction to the ultrasound signals for proper ultrasound image formation and to accommodate the greatly increased number of ultrasound signals/beamforming channels being transmitted between the ultrasound imaging device and the imaging system/processing unit.

SUMMARY OF THE DISCLOSURE

According to one aspect of an exemplary embodiment of the disclosure, an ultrasound system includes a deployable ultrasound device having a transducer including a plurality of transducer arrays or segments spaced apart by a shape memory material, where the segments are configured to transition between a first folded or collapsed shape and a second unfolded or expanded shape. The transitioning of the transducer between the first and second shapes allows dimensions of the transducer's imaging aperture to be modified in response to one or more stimuli. The transducer size may thereby be selectively reduced to allow the transducer to pass through small channels and increased when disposed at a desired location to obtain high resolution data with increased acquisition speed.

The deployable ultrasound imaging device is operably connected to an ultrasound imaging system including a processing unit configured to operate the transducer and the individual segments in order to emit ultrasound signals from the segments and to receive ultrasound signals from the structures surrounding the segments. The ultrasound imaging system/processing unit can process the transmitted and received signals by beamforming to direct the ultrasound signals emitted from the segments in order to provide data for an ultrasound image of the desired structure(s). As a part of the operation of the imaging process, the ultrasound imaging system/processing unit mechanically or acoustically determines the position of the individual segments with regard to one another to determine the position of the segments with regard to one another. Using the determination of the angular and translational position, the ultrasound imaging system/processing unit can apply a beamforming correction to the ultrasound signals emitted from and/or received by the segments based on the position of the segments in order to produce an accurate ultrasound image from the signal data forming the ultrasound image.

The deployable ultrasound imaging device is additionally configured in conjunction with the imaging system/processing unit to accommodate the increased number of individual transducer element signals/channels required for the device. The configurations include processing the signals/channels by multiplexing the channels in order to transmit multiple signals over individual connections between the device and the imaging system/processing unit, or by altering the form of the signals being transmitted to accommodate the increased signal/channel load between the device and the imaging system/processing unit.

According to another aspect of an exemplary embodiment of the present disclosure, a method of determining relative position offsets for transducer segments of an ultrasound device including a number of relatively movable transducer segments includes the steps of providing an ultrasound device including a first transducer segment moveably connected to a second transducer segment via a controllable actuator, moving the first transducer segment relative to the second transducer segment by operating the controllable actuator, determining a positional offset for ultrasound signals emitted from the first transducer segment relative to ultrasound signals emitted from the second transducer segment, and correcting subsequent ultrasound signals emitted from or received by at least one of the first and second transducer segments using the positional offset to produce an ultrasound image.

According to still another aspect of an exemplary embodiment of the present disclosure, a method for forming an ultrasound image includes the steps of providing an ultrasound device with a number of segments each formed of an array of transducer elements, each segment connected to an adjacent segment by a controllable actuator, operating the transducer elements in each segment to emit ultrasound signals, forming a number of segment ultrasound signal data sets by coherently summing the ultrasound signals received by the transducer elements on each segment to form segment ultrasound signals, and incoherently summing the number of segment ultrasound signals to generate the image.

According to still a further aspect of an exemplary embodiment of the present disclosure, a method of transmitting signals from an ultrasound device includes the steps of providing an ultrasound device including a number of segments each formed of an array of transducer elements, each segment connected to an adjacent segment by a controllable actuator and to an application specific integrated circuit (ASIC) that is operably connected to an ultrasound control and display system, receiving a number of ultrasound signals via the transducer elements on each of the number of segments, forming the signals into a number of data channels representing ultrasound signals received by selected transducer elements, and multiplexing the data channels over the connection to the control and display system.

According to another aspect of an exemplary embodiment of the present disclosure, a method of generating an ultrasound image includes the steps of providing an ultrasound device including a number of segments each formed of an array of transducer elements, each segment connected to an adjacent segment by a controllable actuator that forms a gap between transducer elements of adjacent segments, receiving a number of ultrasound signals via the transducer elements on each of the number of segments, modifying ultrasound signals received by transducer elements adjacent the gap to reduce artifacts in an ultrasonic image formed from the ultrasound signals, and combining the adjusted ultrasound signals with the remaining ultrasound signals to generate the ultrasound image.

It should be understood that the brief description above is provided to introduce in simplified form a selection of concepts that are further described in the detailed description and shown in the accompanying drawing figures. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode currently contemplated of practicing the present disclosure.

In the drawings.

DETAILED DESCRIPTION OF THE DRAWINGS

Figure 1:
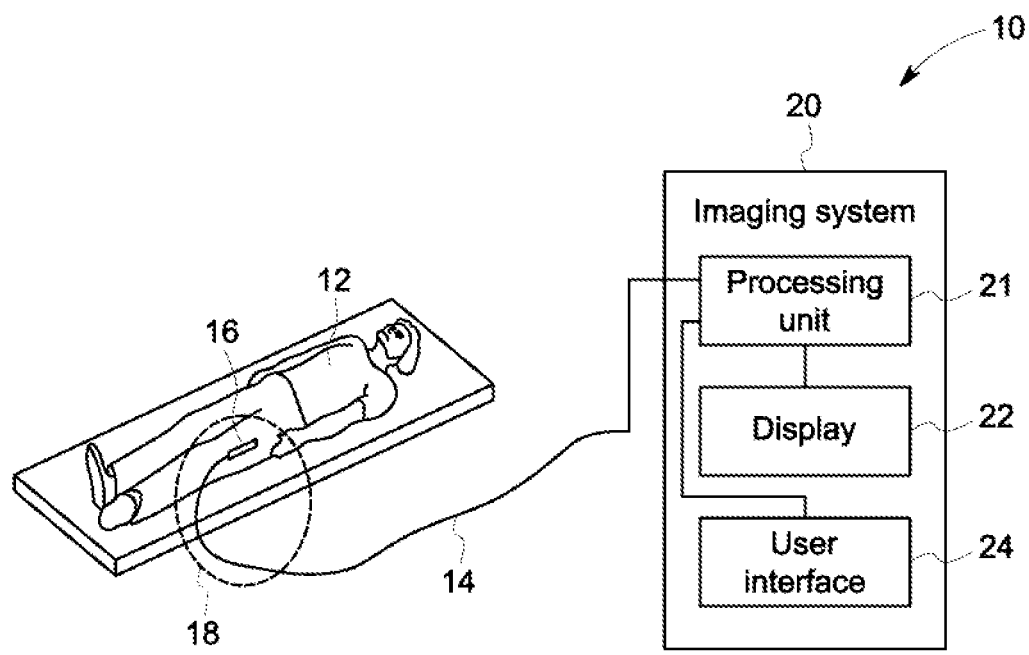
FIG. 1 shows a block diagram of an exemplary ultrasound system including a deployable catheter.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

FIGS. 1-9B show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Medical imaging techniques, such as ultrasound imaging, may be used to obtain real-time data about a patient's tissues, organs, blood flow, etc. However, high resolution data for inner cavities of the tissues and organs may be difficult to obtain via external scanning of the patient. In such instances, a deployable ultrasound imaging device can be a catheter outfitted with an ultrasound device/probe that can be inserted intravenously into the patient and directed to a target site. The deployable catheter may travel through a narrow channel, such as a vein or artery and therefore may have a similar diameter. However, the narrow diameter of the deployable catheter may limit a size of the probe which, in turn, may constrain data quality and acquisition speed provided by the probe. For example, when the probe is an ultrasound probe, a resolution and penetration of the ultrasound probe may be determined by a size of a transducer of the probe and in order to increase image quality of the ultrasound probe, a larger transducer than can be enclosed within a housing of the deployable catheter may be demanded.

In one example, the issues described above may be at least partially addressed by incorporating a shape memory material into the deployable catheter, such as that disclosed in co-owned U.S. Non-Provisional patent application Ser. No. 15/930,302, filed May 12, 2020, entitled Methods And Systems For An Invasive Deployable Device, the entirety of which is expressly incorporated herein by reference for all purposes. The shape memory material may be a shape memory polymer (SMP) configured to alternate between at least two different shapes. A footprint of a transducer of the deployable catheter, where the SMP is coupled to the transducer, may be selectively increased or decreased. The shape-changing behavior of the SMP allows the transducer to have, for example, a first shape with a first set of dimensions enabling the transducer to be readily inserted into the patient's body within the deployable catheter housing. In response to exposure to a stimulus, the SMP may adjust to a second shape with a second set of dimensions that increases a size of the transducer. By subjecting the SMP to a second stimulus, the SMP may be returned to the first shape, thereby decreasing the size of the transducer. In this way, the imaging probe may be maintained small and easily maneuverable within the patient and enlarged when deployed in a target anatomical region to obtain high resolution data. By leveraging the SMP to induce shape transitions, a cost of the deployable catheter may be maintained low while allowing for a large range of deformation.

Turning now to FIG. 1, a block diagram of an exemplary system 10 for use in medical imaging is illustrated. It will be appreciated that while described as an ultrasound imaging system herein, the system 10 is a non-limiting example of an imaging system which may utilize a deployable device to obtain medical images. Other examples may include incorporating other types of invasive probes such as endoscopes, laparoscopes, surgical probes, intracavity probes, amongst others used for imaging internal structures of objects in the medical, material science, structural testing, industrial or other fields. The system 10 may be configured to facilitate acquisition of ultrasound image data from an object, such as a patient 12 via an insertable ultrasound imaging device 14, such as an ultrasound imaging catheter. For example, the ultrasound imaging device 14 may be configured to acquire ultrasound image data representative of a region of interest in the patient 12 such as the cardiac or pulmonary region. In one example, the ultrasound imaging device 14 may be configured to function as an invasive probe. Reference numeral 16 is representative of a portion of the ultrasound imaging device 14 disposed inside the patient 12, such as inserted into a vein. Reference numeral 18 is indicative of a portion of the ultrasound imaging device 14 depicted in greater detail in FIG. 2.

The system 10 may also include an ultrasound imaging system 20 that is in operative association with the ultrasound imaging device 14 and configured to facilitate acquisition of ultrasound image data. It should be noted that although the exemplary embodiments illustrated hereinafter are described in the context of a medical imaging system, such as an ultrasound imaging system, other imaging systems and applications are also contemplated (e.g., industrial applications, such as nondestructive testing, borescopes, and other applications where ultrasound imaging within confined spaces may be used). Further, the ultrasound imaging system 20 may include a processing device 21 that is configured utilize output signals/channels from the ultrasound imaging device 14 to create ultrasound images and to display an image representative of a current position of the imaging catheter tip within the patient 12. As illustrated in FIG. 1, the ultrasound imaging system 20 may include a display area 22 and a user interface area 24. In some examples, the display area 22 of the ultrasound imaging system 20 may be configured to display a two- or three-dimensional image generated by the ultrasound imaging system 20 based on the image data acquired via the ultrasound imaging device 14. For example, the display area 22 may be a suitable CRT or LCD display on which ultrasound images may be viewed. Alternatively, the ultrasound image may be displayed on a wirelessly connected mobile device (not shown) like a smartphone or tablet. The user interface area 24 may include an operator interface device configured to aid the operator in identifying a region of interest to be imaged and to control the operation of the ultrasound imaging device 14. The operator interface may include a keyboard, mouse, trackball, joystick, touch screen, voice or haptic control or any other suitable interface device.

Figure 2:
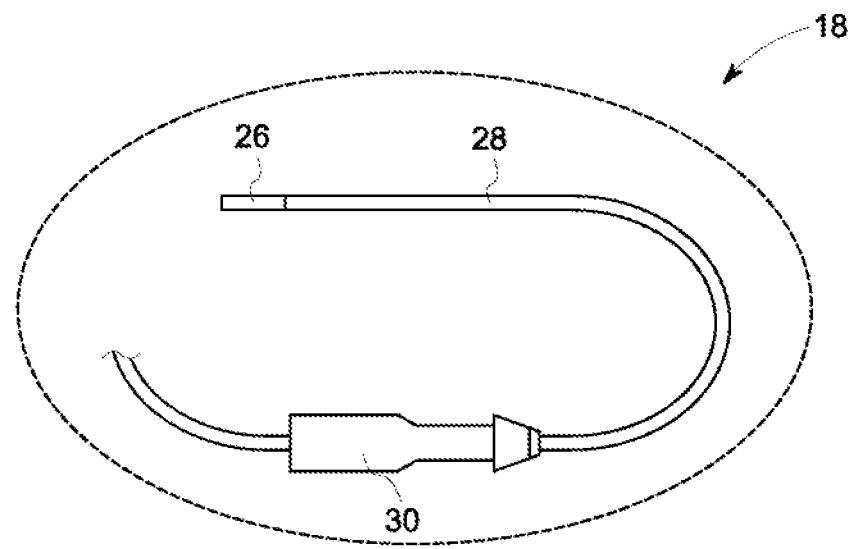
FIG. 2 shows the deployable catheter of FIG. 1 in greater detail, including an exemplary imaging catheter tip and transducer for use in the system illustrated in FIG. 1.

FIG. 2 illustrates an enlarged view of the portion 18 shown in FIG. 1 of the ultrasound imaging device 14. As depicted in FIG. 2, the ultrasound imaging device 14 may include a tip 26 on a distal end of a flexible shaft 28. The catheter tip 26 may house a transducer and motor assembly. The transducer may include one or more transducer arrays, each transducer array including one or more transducer elements. The ultrasound imaging device 14 may also include a handle 30 configured to facilitate an operator manipulating the flexible shaft 28.

Figure 3:
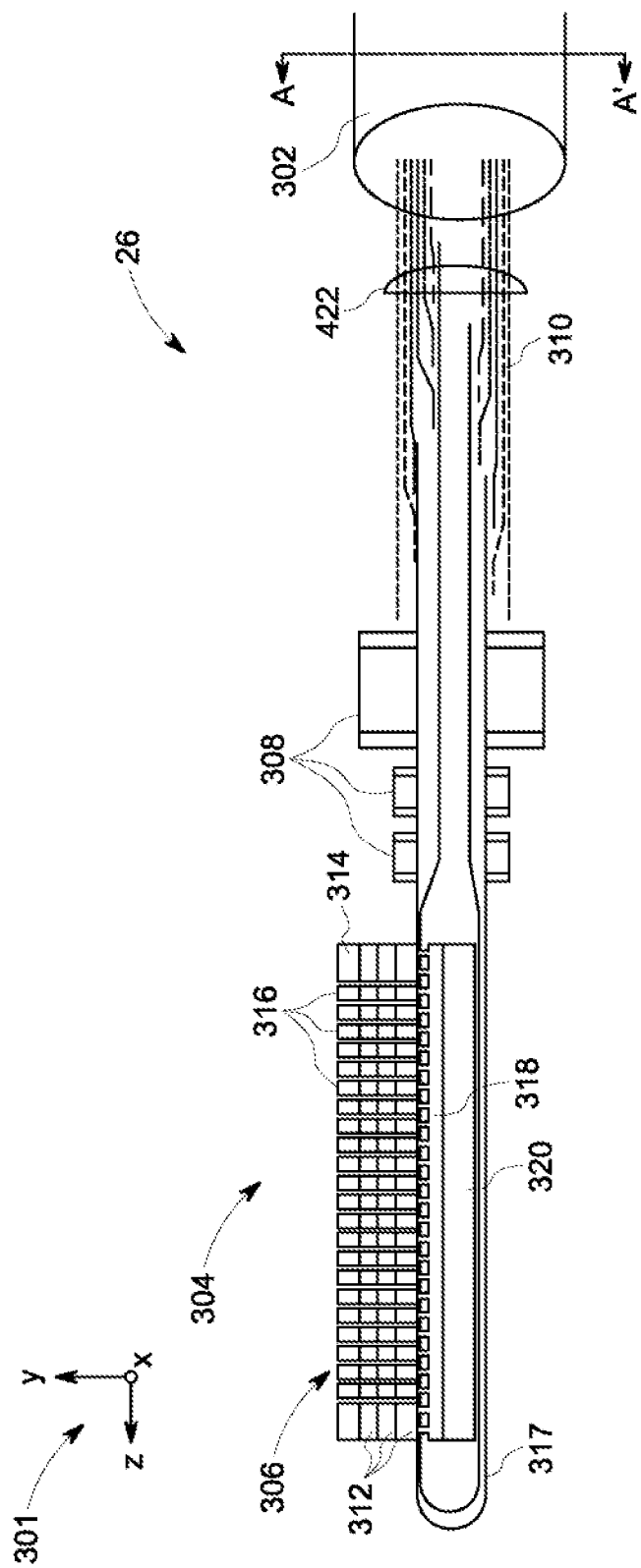
FIG. 3 shows a first cross-sectional view of the exemplary imaging catheter tip which may be included in the deployable catheter of FIG. 2.

An example of the catheter tip 26 of FIG. 2 is shown in FIG. 3. A set of reference axes 301 are provided, indicating a y-axis, an x-axis, and a z-axis. The catheter tip 26 may have a housing 302 surrounding a transducer 304 which may include at least one transducer array 306, capacitors 308, and a catheter cable 310 connecting the transducer 304 to the imaging system 20/processing unit 21. The other components not shown in FIG. 3 may also be enclosed within the housing 302, such as a motor, a motor holder, a thermistor, and an optional lens, for example. Furthermore, in some examples, the catheter tip 26 may include a system for filling the tip with a fluid, such as an acoustic coupling fluid.

The transducer array 306 has several layers stacked along the y-axis and extending along the x-z plane. One or more layers of the transducer array 306 may be layers of transducer elements 312. In one example, the transducer elements 312 may be piezoelectric elements, where each piezoelectric element may be a block formed of a natural material such as quartz, or a synthetic material, such as lead zirconate titanate, that deforms and vibrates when a voltage is applied by, for example, a transmitter. In some examples, the piezoelectric element may be a single crystal with crystallographic axes, such as lithium niobate and PMN-PT ($Pb(Mg_{1/3}Nb_{2/3})O_3$—$PbTiO_3$). The vibration of the piezoelectric element generates an ultrasonic signal formed of ultrasonic waves that are transmitted out of the catheter tip 26. The piezoelectric element may also receive ultrasonic waves, such as ultrasonic waves reflected from a target object, and convert the ultrasonic waves to a voltage. The voltage may be transmitted to a receiver of the imaging system and processed into an image. The transducer may also be fabricated as a cMUT (capacitive micromachined ultrasound transducer) or a pMUT (piezoelectric micromachined ultrasound transducer).

An acoustic matching layer 314 may be positioned above the transducer elements 312. The acoustic matching layer 314 may be a material positioned between the transducer elements 312 and a target object to be imaged. By arranging the acoustic matching layer 314 in between, the ultrasonic waves travel with less reflections inside the transducer and couple better from the transducer to the target medium. The acoustic matching layer 314 may shorten a pulse length of the ultrasonic signal, thereby increasing an axial resolution of the signal.

The layers formed by the acoustic matching layer 314 and the transducer elements 312 may be diced along at at least one of the y-x plane and the y-z plane to form individual acoustic stacks 316. Dicing at both the y-x and y-z planes creates a matrix transducer for 3D/4D imaging. Each of the acoustic stacks 316 may be electrically insulated from adjacent acoustic stacks but may all be coupled to at least one common layer positioned below or above the transducer elements, with respect to the y-axis. In some implementations, an acoustic dematching layer (DML) maybe positioned in-between the transducer elements and the ASIC.

The DML is characterized by an acoustic impedance as high as possible (typically 2-5 times higher than the impedance of the transducer).

An electrical circuit 318 may be layered below, relative to the y-axis, the transducer elements 312. In one example, the electrical circuit may be at least one application-specific integrated circuit (ASIC) 318 directly in contact with each of the acoustic stacks 316. Each ASIC 318 may be coupled to one or more flex circuits 317 which may extend continuously between the transducer array 306 and the catheter cable 310. The flex circuits 317 may be electrically coupled to the catheter cable 310 to enable transmission of electrical signals between the transducer array 306 and an imaging system, e.g., the imaging system 20/processing device 21 of FIG. 1, to enable the controlled operation of the elements 312 of the array 306 by the imaging system 20/processing unit 21 and the formation of ultrasound images by the imaging device 20/processing unit 21 using the output signals from the transducer elements 312/channels. The electrical signals may be tuned by the capacitors 308 during transmission. The flex circuits 317 may be positioned in-between the transducer elements and ASIC or on the opposite side of the ASIC or next to the ASIC. Appropriate electrical connection methods (e.g. solder or compressional bonding, anisotropic films or pastes) are applied to connect signals from the flex circuit to the ASIC and vice versa. The transducer elements may be bonded to the ASIC with wafer level bonding methods.

An acoustic backing layer 320 may be arranged below the ASIC 318, with respect to the z-axis. In some examples, as shown in FIG. 3, the backing layer 320 may be a continuous layer of material that extends along the x-z plane. The backing layer 320 may be configured to absorb and attenuate backscattered waves from the transducer elements 312. A bandwidth of an acoustic signal generated by the transducer elements 312, as well as the axial resolution, may be increased by the backing 320.

As described above, the transducer 30, the capacitors 308, and the catheter cable 310 may be enclosed within the housing 302. Thus a size, e.g., a diameter or width of the components may be determined by an inner diameter of the housing 302. An inner diameter of the housing 302 may be, in turn, determined by an outer diameter and a desirable thickness of the housing 302. The outer diameter of the housing 302 may be constrained by a region of a patient's body through which the imaging catheter is inserted. For example, the imaging catheter may be an intracardiac echocardiography (ICE) catheter used to obtain images of cardiac structures and blood flow inside the patient's heart.

The imaging catheter may be introduced into the heart through the aorta, inferior vena cava, or jugular vein. In some instances, the imaging catheter may be fed through regions with narrower diameters, such as the coronary sinus, the tricuspid valve, and the pulmonary artery. As such, the outer diameter of the imaging catheter may not be greater than 10 Fr or 3.33 mm. The outer diameter and corresponding inner diameter of the imaging catheter housing are shown in FIG. 4 in a cross-section 400 of the housing 302 of the catheter tip 26, taken along line A-A' depicted in FIG. 3.

Figure 4:
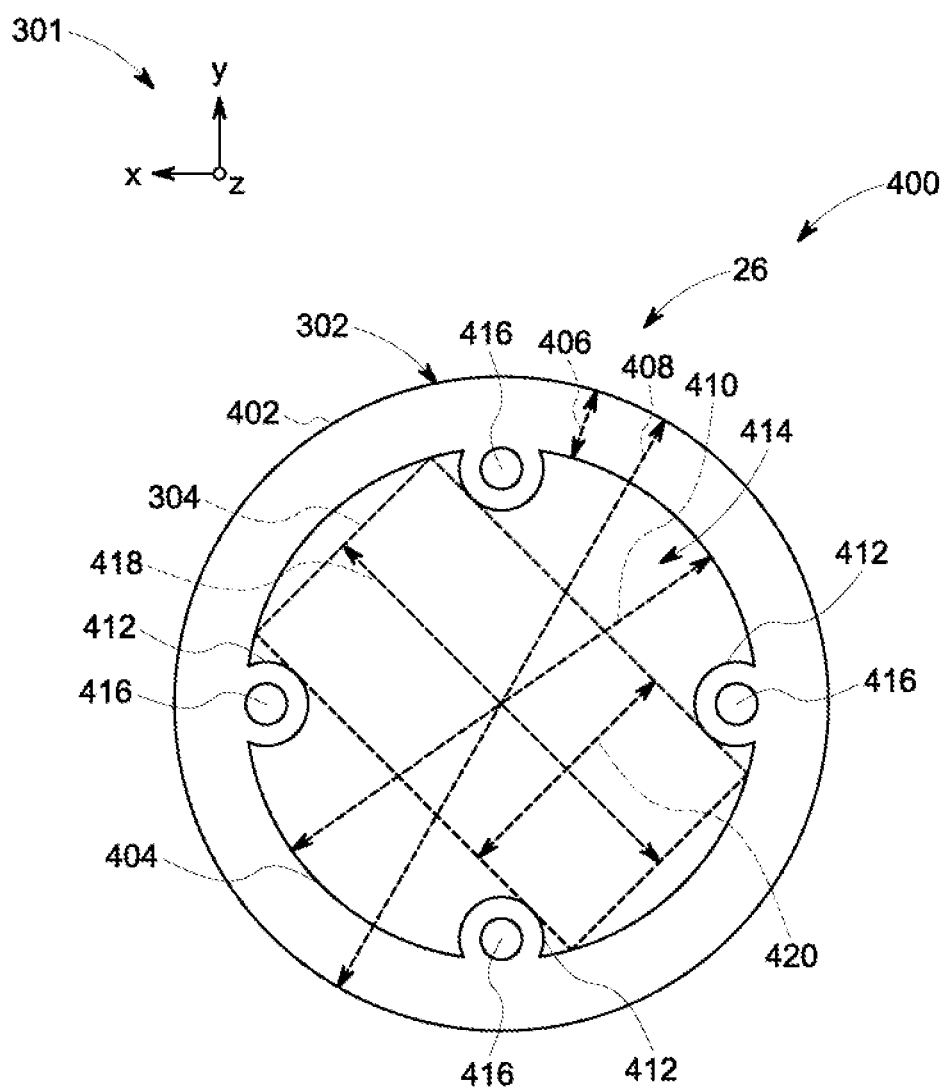
FIG. 4 is a schematic of a second cross-sectional view of the deployable catheter of FIG. 2.

As shown in FIG. 4, an outer surface 402 of the housing 302 of the ultrasound imaging device may be spaced away from an inner surface 404 of the housing 302 by a thickness 406 of the housing 302. The thickness 406 of the housing 302 may be optimized to provide the housing 302 with a target degree of structural stability, e.g. resistance to deformation, balanced with flexibility, e.g., ability to bend when a force is applied. In one example, an outer diameter 408 of the housing 302 may be 3.33 mm, the thickness 406 may be 0.71 mm, and an inner diameter 410 of the housing 302 may be 2.62 mm. In other examples, the outer diameter of the housing may be between 2-5 mm, the thickness may be between 0.24-1 mm, and the inner diameter may be between 1-4 mm. In yet other examples, the imaging catheter may have a variety of dimensions, depending on application. For example, an endoscope may have an outer diameter 10-12 mm. It will be appreciated that the imaging catheter may have various diameters and sizes without departing from the scope of the present disclosure.

The inner surface 404 of the housing 302 may include lobes 412 protruding into an inner volume, or lumen 414 of the housing 302. The lobes 412 may be semi-circular projections, each enclosing an individual lumen 416 for housing a steering wire of the imaging catheter. An arrangement of the transducer 304 of the imaging catheter within the lumen 414 of the housing 302 is indicated by a dashed rectangle. A maximum elevation aperture 418 of the transducer 304 may be determined based on the inner diameter 410 of the housing 302 and a height 420 of the transducer 304 may be configured to fit between the lobes 412 of the housing 302. In one example, the elevation aperture 418 may be a maximum of 2.5 mm and the height 420 may be a maximum of 1 mm.

As described above, dimensions of the transducer 304 may be determined by the inner diameter 410, thickness 406, and outer diameter 408 of the housing 302 which may, in turn, be determined based on insertion of the imaging catheter into specific regions of the patient's anatomy. The constraints imposed on a size of the transducer 304 and diameter 422 (FIG. 3) of the catheter cable, may affect a resolution, penetration, and fabrication of the transducer 304. Each of the resolution, penetration and ease of fabrication may be enhanced by increasing the size of the transducer 304 but the geometry of the transducer 304, and therefore performance, is bound by the dimensions of the catheter housing 302 in order for the deployable catheter to travel intravenously through a patient.

In one example, the transducer may be enlarged upon deployment at a target site by adapting the transducer with a shape memory material. The shape memory material may be a shape memory polymer (SMP) configured to respond mechanically to one or more stimuli. Examples of SMPs include linear block copolymers, such as polyurethanes, polyethylene terephthalate, polyethyleneoxide, and other thermoplastic polymers such as polynorbornene. In one example, the SMP may be a powder mixture of silicone and tungsten in an acrylic resin. The SMP may be stimulated by physical stimuli, such as temperature, moisture, light, magnetic energy, electricity, etc., by chemical stimuli, such as chemicals, pH level, etc., and by biological stimuli, such as presence of glucose and enzymes. When applied to an imaging catheter, the transducer may incorporate the SMP to enable a shape of the transducer to be altered upon exposure to at least one stimulus. The SMP may have physical properties as provided below in Table 1 which may offer more desirable characteristics than other types of shape memory materials, such as shape memory alloys. For example, SMPs may have a higher capacity for elastic deformation, lower cost, lower density, as well as greater biocompatibility and biodegradability. In particular, the lower cost of SMPs may be desirable for application in disposable deployable catheters.

TABLE 1

Physical Properties of Shape Memory Polymers

| Property | Range |
|---|---|
| Density (g/cm$^3$) | 0.2-3 |
| Extent of deformation | Up to 800% |
| Required stress for deformation (MPa) | 1-3 |
| Stress generated upon recovery (MPa) | 1-3 |
| Transition temperature (° C.) | −10 to 100 |
| Recovery speed | 1 s to 1 hr |
| Processing condition | <200° C.; low pressure |
| Cost | <$10/lb |

In one example, the SMP may have two-way shape memory so that the SMP may adjust between two shapes without demanding reprogramming or application of an external force. For example, the SMP may convert to a temporary shape in response to a first stimulus and revert to a permanent shape in response to a second stimulus. The first and second stimuli may be of a same or different type, e.g., the first stimulus may be a high temperature and the second stimulus may be a low temperature or the first stimulus may be a humidity level and the second stimulus may be a threshold temperature which can be allied to the SMP by a heat source or other stimuli-applying device (not shown) operably connected to and controlled by the imaging device 20/procession unit 21, optionally under the direction of the user via the user interface 24. The two-way shape memory behavior is neither mechanically nor structurally constrained, thereby allowing the SMP to switch between the temporary shape and permanent shape without applying the external force.

Figure 5:
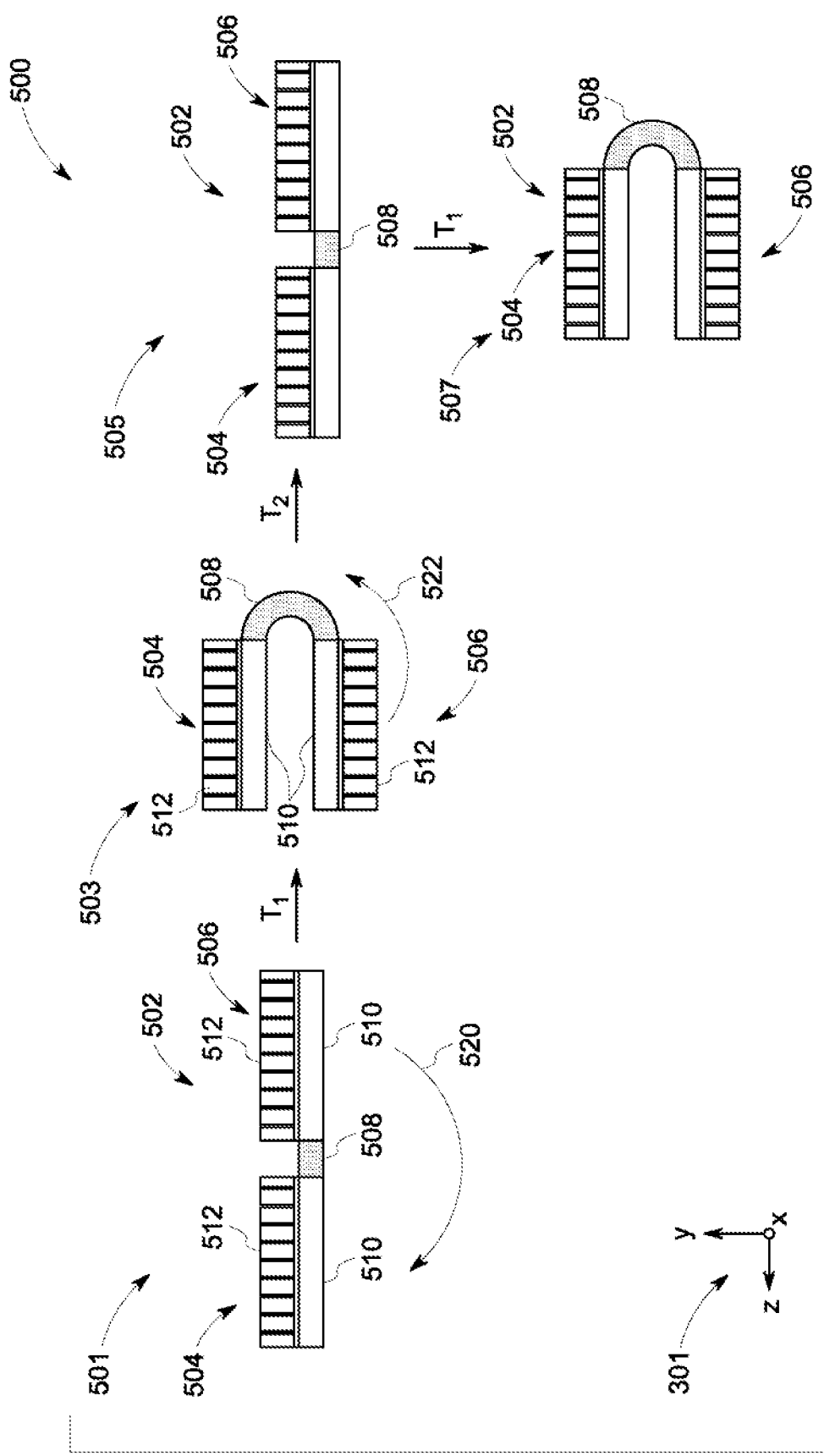
FIG. 5 is a first diagram showing a two-way shape memory effect of a transducer incorporating a shape memory material.

As an example, conversion of a transducer 502 between a first shape and a second shape is shown in a first diagram 500 in FIG. 5. The transducer 502 includes a first transducer array or segment 504 and a second transducer array or segment 506 where the second transducer array 506 is aligned with the first transducer array 504 along the z-axis and spaced away from the first transducer array 504 by the SMP 508. In other words, the transducer 502 has an overall planar shape with the first and second transducer arrays 504, 506 co-planar with one another along a common plane, e.g., the x-z plane. A first step 501 of the first diagram 500, depicts coupling of an SMP 508 to a backing layer 510 of each of the first and second transducer arrays 504, 506. The SMP 508, configured as a two-way memory SMP, is arranged between the transducer arrays along the z-axis and may be fixedly attached to edges of the backing layers 510 and arranged co-planar with the backing layers 510. For example, the backing layers 510 and the SMP 508 arranged therebetween may form a continuous, planar unit. Transducer elements 512 are laminated onto the backing layer 510 of the first and second transducer arrays 504, 506.

In some examples, the SMP 508 may form a continuous layer entirely across the transducer 502. The SMP 508 may form an acoustic layer of the transducer 502, such as a matching layer or a backing layer. By incorporating the SMP 508 as an acoustic layer, an assembly and number of components of the transducer array may be simplified without adversely affecting a reduction in the transducer array footprint.

The transducer 502 is exposed to a first temperature, $T_1$, and, at a second step 503, the SMP 508 changes shape in response to $T_1$. The SMP 508 may bend into a semi-circular shape, pivoting the second transducer array 506 substantially through 180 degrees along a first rotational direction, e.g., clockwise, as indicated by arrow 520. Bending, as referred to herein, may be any transitioning of a planar structure to a non-planar conformation. As such, various deformations of the structure from a configuration that is aligned with a plane may be considered bending.

When the SMP 508 bends, the transducer 502 may therefore also bend. While the SMP may bend through a range of angles, bending of the SMP so that two regions of the transducer 502 become stacked over one another and substantially parallel with one another is referred to as folding herein. The SMP, in some examples, may not bend to an extent that the transducer is folded. However, folding of the transducer may provide a most compact conformation of the transducer to enable passage of the deployable catheter through intravenous passages.

As a result of the folding of the transducer 502, the second transducer array or segment 506 is positioned under the first transducer array or segment 504, with respect to the y-axis, in a folded shape. An overall surface area of the transducer elements 512, including the transducer elements 512 of both the first and second transducer arrays or segments 504, 506, is reduced at the second step 503 compared to the first step 501 when viewing the transducer 502 along the y-axis.

The transducer 502 is exposed to a second temperature, $T_2$, and, in response, the SMP 508 reverts to the planar geometry of the first step 501 at a third step 505 of the first diagram 500. The second transducer array 506 is pivoted substantially through 180 degrees along a second rotational direction, opposite of the first rotational direction, e.g., counterclockwise. The second temperature $T_2$ may be a higher or lower temperature than $T_1$. Subjecting the transducer 502 to $T_1$ again compels the SMP 508 to bend, folding the transducer 502 so that the second transducer array 506 is pivoted 180 degrees at a fourth step 507.

The steps shown in the first diagram 500 may be repeated many times. For example, prior to insertion of an imaging catheter adapted with the transducer 502 of FIG. 5 into a patient, the transducer 502 may be initially exposed to $T_1$ as directed by the imaging system 20/processing device 21 and/or the user via interface 24, to fold and decrease the size of the transducer 502. The folded transducer 502, may fit within a housing of the imaging catheter and inserted intravenously into the patient. When the transducer 502 reaches a target site within the patient, the transducer 502 may be unfolded and enlarged by subjecting the array to $T_2$, as directed by the imaging system 20/processing device 21 and/or the user via interface 24. Images may be obtained while the transducer 502 is unfolded and increased in size. For example, unfolding the transducer 502 may increase an elevation aperture of the transducer 502.

When scanning is complete, the transducer 502 may be exposed again to $T_1$, as directed by the imaging system 20/processing device 21 and/or the user via interface 24, to cause the transducer 502 to fold and decrease in size. The imaging catheter may then be withdrawn from the site and removed from the patient or deployed to another site for imaging within the patient. Thus, the shape and size of the transducer 502 may be adjusted between the planar and folded configurations numerous times during an imaging session.

It will be appreciated that the configurations and operation of the transducer 502 shown in FIG. 5 are non-limiting examples of shapes that the transducer may transition between. Other examples may include the transducer 502 being in a non-planar geometry at the first step 501, such as slightly bent shape, becoming more bent at the second step 503, and alternating between the less bent and more bent shapes upon exposure to one or more stimuli as directed by the imaging system 20/processing device 21 and/or the user via interface 24. In addition, the transducer 502 may fold so that the first and second transducer arrays or segments 504, 506, are not parallel with one another. In yet other examples, the first and second transducer arrays or segments 504, 506 may be different sizes.

Furthermore, when the SMP 508 forms an entire layer across the transducer 502, rather than forming a section between the backing layers 510 of the first and second transducer arrays or segments 504, 506, the SMP 508 may be adapted to change shape only in an area between the transducer arrays. In one example the SMP 508 may be able to change shape via more than one type of transition. For example, the SMP 508 may bend upon exposure to one type of stimulus and shrink upon exposure to another type of stimulus. In another example, the SMP 508 may include more than one type of shape memory material. As an example, the SMP 508 may be formed of a first type of material configured to bend and a second type of material configured to shrink. Other variations in shape transitions, combination of materials, and positioning of the SMP 508 within the transducers have been contemplated.

While temperature changes are described as a stimulus for inducing changes in the SMP shape for the first diagram 500 of FIG. 5, it will be appreciated that the first diagram 500 is a non-limiting example of how deformation of the SMP may be triggered. Other types of stimuli, such as humidity, pH, UV light, etc. may be used to induce mechanical changes in the SMP. More than one type of stimulus may be applied to the SMP to achieve similar or different shape modification as directed by the imaging system 20/processing device 21 and/or the user via interface 24. Furthermore, deformation of the SMP may include other manners of shape change other than bending. For example, the SMP may curl into a jellyroll configuration or shrink along at least one dimension. Details of the mechanical deformation and stimuli used to elicit the deformation are described further below.

Figure 6A:
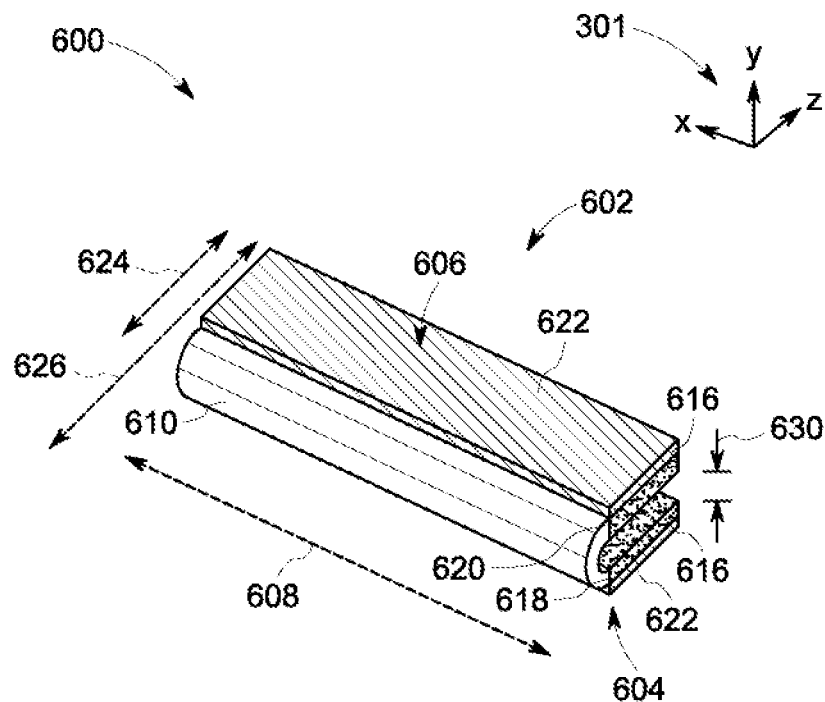
FIG. 6A shows a first example of a transducer adapted with the shape memory material in a folded configuration.
Figure 6B:
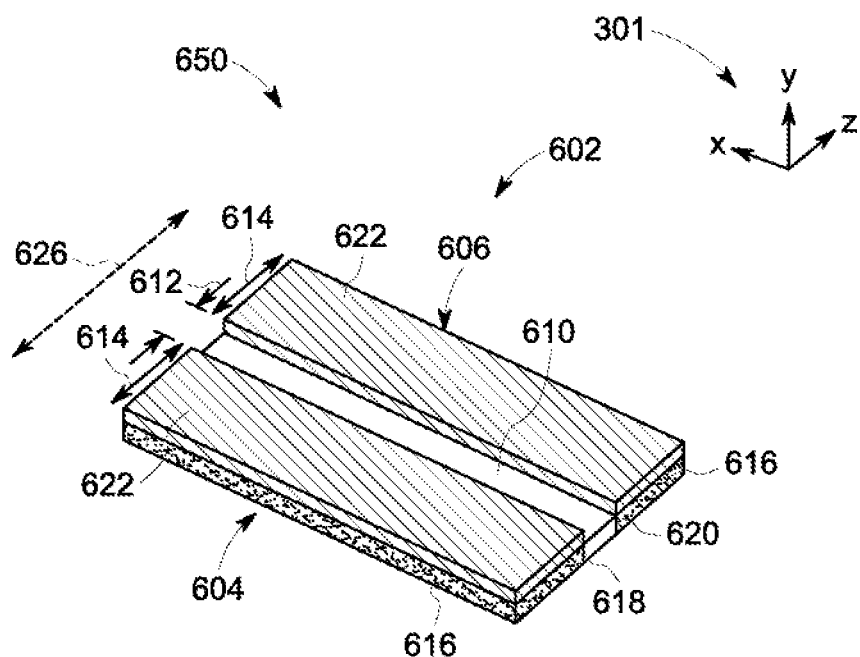
FIG. 6B shows the first example of the transducer of FIG. 6A in an unfolded configuration.

In some examples, as shown in FIG. 5, a transducer 502 of a deployable catheter may include two sections, or two transducer arrays or segments 504,506. Each transducer array/segment 504,506 may include one or more acoustic stacks, including, as described above with reference to FIG. 3, a matching layer, an element, and a backing layer. An ASIC may be coupled to each transducer array/segment 504,506 as also illustrated and described with regard to FIG. 3. A first example of a transducer 602 incorporating a SMP to enable modification of an active area of the transducer 602 is shown in FIGS. 6A and 6B. The transducer 602 can be operated in a manner similar to embodiments described previously, and is shown in a first, folded configuration 600 in FIG. 6A and in a second, unfolded configuration 650 in FIG. 6B.

The transducer 602 has a first transducer array or segment 604 and a second transducer array or segment 606. The first and second transducer arrays or segments 604, 606 have similar dimensions and are each rectangular and longitudinally aligned with the x-axis, e.g., a length 608 of each transducer array is parallel with the x-axis. A SMP 610 is arranged between the transducer arrays, along the z-axis. In other words, the first transducer array 604 is spaced away from the second transducer array 606 by a width 612 of the SMP 610, as shown in FIG. 6B. The width 612 of the SMP 610 may be less than a width 614 of each of the first and second transducer arrays 604, 606 while a length of the SMP 610, defined along the x-axis, may be similar to the length 608 of the transducer arrays.

The SMP 610 may be connected to inner edges of a backing layer 616 of each of the first and second transducer arrays or segments 604, 606. For example, the SMP 610 may be directly in contact with and adhered to a longitudinal inner edge 618 of the backing layer 616 of the first transducer array 604, e.g., an edge of the backing layer 616 facing the second transducer array 606 and aligned with the x-axis, and to a longitudinal inner edge 620 of the backing layer 616 of the second transducer array 606, e.g., an edge of the backing layer 616 facing the first transducer array 604 and aligned with the x-axis. A thickness of the SMP 610 may be similar to a thickness of the backing layer 616 of each of the first and second transducer arrays 604, 606, the thicknesses defined along the y-axis. A matching layer 622 is stacked above the backing layer 616 of each of the transducer arrays. An element, e.g., a piezoelectric element, may be arranged between the matching layer 622 and the backing layer 616 (not shown in FIGS. 6A and 6B).

When in the first configuration 600 as shown in FIG. 6A, the SMP 610 is curved into a semi-circular shape. The second transducer array or segment 606 is stacked directly over, with respect to the y-axis, and spaced away from the first transducer array segment 604, so that both transducers are maintained co-planar with the x-z plane. The transducer 602 is folded in FIG. 6A so that each matching layer 622 of the transducer arrays face away outwards and away from one another and the backing layers 616 of the transducer arrays face one another. The backing layers 616 may be spaced away from one another by a distance 630 similar to a diameter of the semi-circle formed by the SMP 610. However, in other examples, the transducer 602 may be folded in an opposite direction so that the backing layers 616 of the transducer arrays face one another and the matching layers 622 face away from one another.

As the transducer 602 transitions between the first and second configurations 600, 650, at least one of the transducer arrays are pivoted, for example, 180 degrees relative to the other transducer array. For example, when adjusting from the first configuration 600 to the second configuration 650, the first transducer array 604 may be pivoted through a first rotational direction to become co-planar with the second transducer array 606. Alternatively, the second transducer array 606 may be pivoted 180 degrees through a second rotational direction, opposite of the first rotational direction. The first transducer array 604 may be pivoted through the second rotational direction or the second transducer array 606 may be pivoted through the first rotational direction to return the transducer 602 to the first configuration 600. In another example, both transducer arrays may be pivoted through 90 degrees to achieve transitioning between the first and second configurations 600, 650. It will be appreciated that description of the pivoting of the transducer arrays through 180 degrees is for illustrative purposes and other examples may include the transducer arrays or segments pivoting more or less than 180 degrees.

In the first configuration 600, a width 624 of the transducer 602 is reduced relative to a width 626 of the transducer 602 in the second configuration 650. An active area of the transducer 602 may be equal to a surface area of one of the first or second transducer arrays or segments 604, 606. In the second configuration 650, with the first and second transducer arrays or segments 604, 606 co-planar with one another and side-by-side, the active area of the transducer 602 is doubled relative to the first configuration 600. As such, an elevation aperture of the transducer 602 is at least doubled when unfolded into the second configuration 650, thereby increasing a resolution and penetration of the transducer 602.

In another example, a transducer of an imaging probe may include more than two segments or transducer arrays. A second example of a transducer 702 that can be operated in a manner similar to embodiments described previously is shown in a first, folded configuration 700 in FIGS. 7A and 7C, and a second, unfolded configuration 750 in FIG. 7B. The transducer 702 includes a first transducer array or segment 704, a second transducer array or segment 706, and a third transducer array or segment 708. All three transducer arrays or segments may have similar dimensions and geometries and may be connected by a first SMP 710 and a second SMP 712.

Figure 7A:
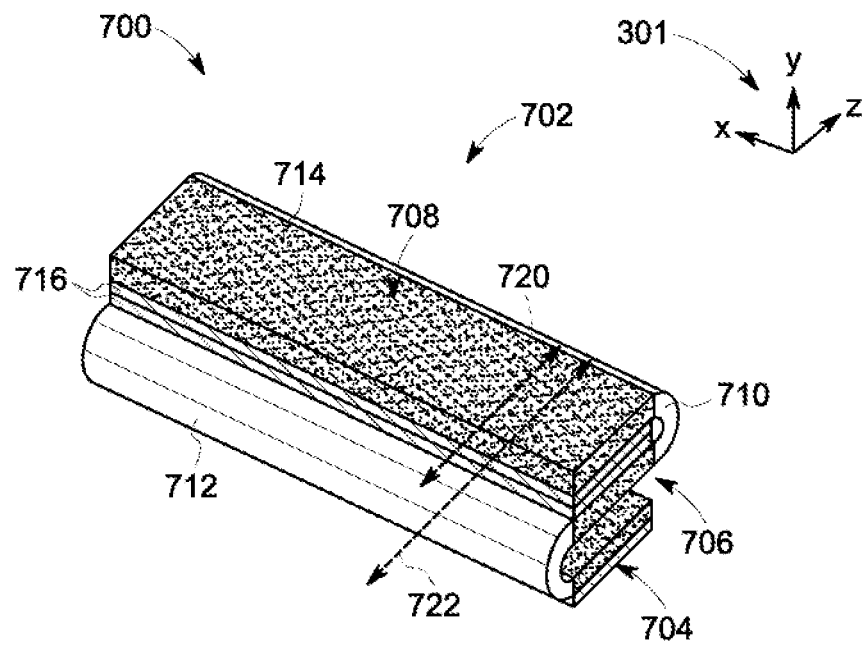
FIG. 7A shows a second example of a transducer adapted with a shape memory material in a folded configuration.
Figure 7B:
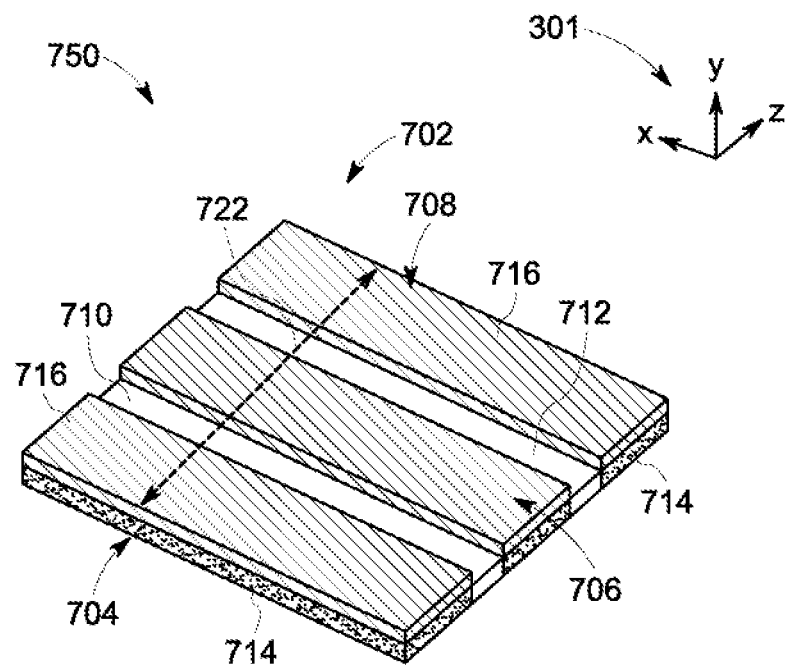
FIG. 7B shows the second example of the transducer of FIG. 7A in an unfolded configuration.

For example, the transducer arrays or segments may be spaced away from one another but co-planar and aligned along the x-axis and z-axis in the second configuration 750 of FIG. 7B. The first transducer array or segment 704 is spaced away from the second transducer array segment 706 by the first SMP 710 and the second transducer array segment 706 is spaced away from the third transducer array or segment 708 by the second SMP 712. As described above for the first example of the transducer 602 of FIGS. 6A-6B, the SMPs may be directly connected to longitudinal inner edges of the transducer arrays along a backing layer 714 of each transducer array. The SMPs may be co-planar and have a similar thickness to the backing layer 714 of the transducer arrays. A matching layer 716 of each of the transducer arrays is positioned above the backing layer 714 and aligned with each backing layer 714 along the y-axis. As such, the matching layer 716 protrudes above the first and second SMPs 710, 712 with respect to the y-axis. An element may be arranged between the matching layer 716 and the backing layer 714 (not shown in FIGS. 7A and 7B).

Figure 7C:
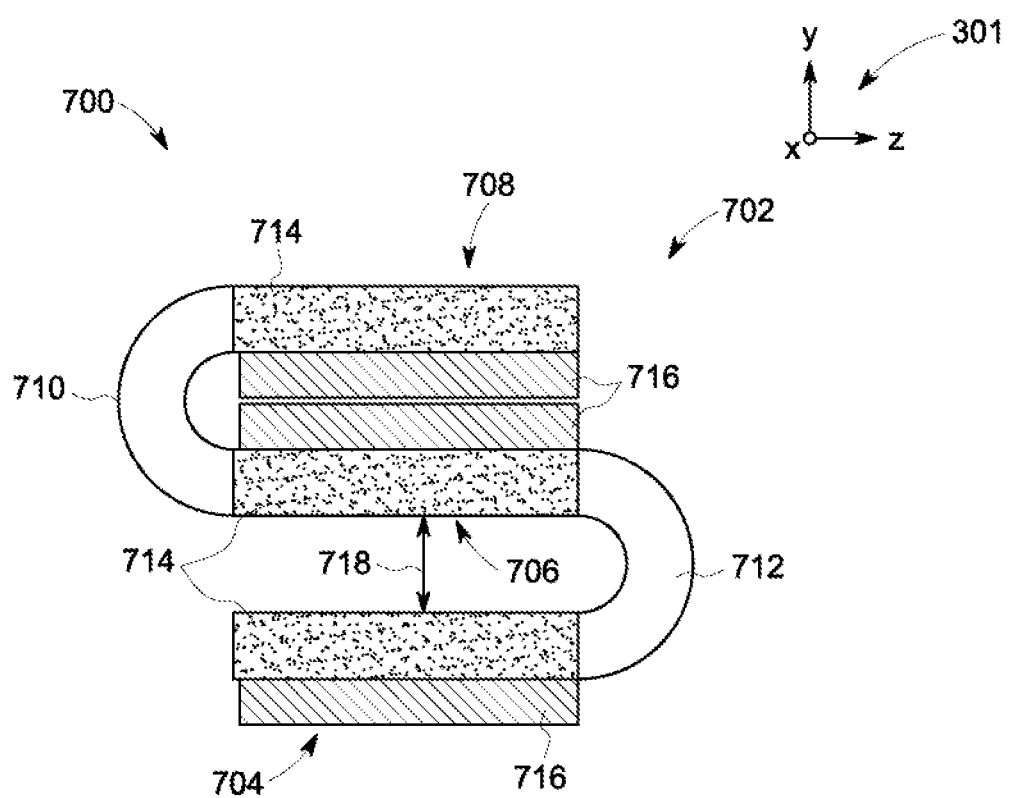
FIG. 7C shows another view of the second example of the transducer of FIG. 7A in the folded configuration.

In the first configuration 700 of FIG. 7A, the transducer 702 is folded into an S-shaped geometry when viewed along the x-axis, as shown in FIG. 7C. In the S-shaped geometry, the first SMP 710 is bent into a semi-circle, forming a right half of a circle. The first transducer array or segment 704 may be pivoted through a first rotational direction relative to the second transducer array or segment 706 so that the second transducer array or segment 706 is stacked over and aligned with the first transducer array segment 704 with respect to the y-axis. While the backing layer 714 of the second transducer array segment 706 and the backing layer 714 of the first transducer array segment 704 face each other with no other component of the transducer 702 positioned therebetween, the backing layer 714 of the transducer arrays are spaced apart by a distance 718 similar to a diameter of the semi-circle formed by the first SMP 710.

The second SMP 712 is bent in an opposite direction from the first SMP 710, into a semi-circle forming a left half of a circle. The bending of the second SMP 712 causes the third transducer array or segment 708 to be stacked over the second transducer array or segment 706 along the y-axis. The third transducer array or segment 708 is pivoted through a second rotational direction, opposite of the first rotation direction, so that the third transducer array segment 708 is aligned with both the first and second transducer arrays or segments 704, 706, along the y-axis and the matching layer 716 of the third transducer array or segment 708 faces the matching layer 716 of the second transducer array 706. The matching layers 716 of the second and third transducer arrays or segments 706, 708 are separated by a gap that is smaller than the distance 718 between the backing layers 714 of the first and second transducer arrays or segments 704, 706.

As the transducer 702 transitions between the first and second configurations 700, 750, at the first and third transducer arrays 704, 708, may be pivoted through 180 degrees in opposite rotation directions, relative to the second transducer array 706. For example, when adjusting from the first configuration 700 to the second configuration 750, the first transducer array 704 may be pivoted through a first rotational direction to become co-planar with the second transducer array 606. The third transducer array 708 may be pivoted through a second rotational direction, opposite of the first rotational direction to also become co-planar with the second transducer array 606. To return the transducer 702 to the first configuration 700 from the second configuration 750, the first transducer array 704 may be pivoted 180 degrees through the second rotational direction and the second transducer array 706 may be pivoted 180 degrees through the first rotational direction. Alternatively, on other examples, the transducer arrays may be pivoted opposite of the transitioning described above. It will be appreciated that description of the pivoting of the transducer arrays through 180 degrees is for illustrative purposes and other examples may include the transducer arrays pivoting through more or less than 180 degrees.

A width 720, as shown in FIG. 7A, of the transducer 702 in the first configuration 700 may be narrower than a width 722 of the transducer 702 in the second configuration 750. An active area of the transducer 702, determined by a total transducer array surface area along the x-z plane, may be increased threefold when the transducer 702 is adjusted from the first configuration 700 to the second configuration 750. Thus, when a transducer is formed of three segments or transducer arrays (a 3-section transducer, hereafter), and the unfolded 3-section transducer, e.g., the second configuration 750 of FIG. 7B, is equal in size to an unfolded transducer with two segments or transducer arrays (a 2-section transducer, hereafter), e.g., the second configuration 650 of FIG. 6B, the transducer arrays of the 3-section transducer may be narrower in width than the transducer arrays of the 2-section transducer. When folded, the 3-section transducer may have a smaller footprint than the 2-section transducer and may thereby be inserted through narrower channels.

Alternatively, the segments or transducer arrays of the 3-section and 2-section transducers may be similar in size. When folded, both the transducers may have a similar footprint. However, when deployed and unfolded in a target scanning site, the 3-section transducer may have a larger active area, allowing the 3-section transducer to have greater resolution and penetration than the 2-section transducer. Furthermore, the first and second examples of the transducer shown in FIGS. 6A-7C are non-limiting examples. Other examples may include transducers with more than three segments, or transducers and segments/transducer arrays with different geometries and dimensions from those shown.

The folding of a transducer compelled by an SMP, as illustrated in FIGS. 5-7C, may be leveraged to allow the transducer to be implemented in a deployable catheter, such as the imaging catheter 14 of FIG. 1, without inhibiting passage of the deployable catheter through narrow arteries and veins. For example, as shown in a perspective view 800 in FIG. 8A and an end view 850 in FIG. 8B, the transducer 702 of FIGS. 7A-7C may be employed in a catheter tip 802. In one example, the catheter tip 802 may be the catheter tip 26 of FIGS. 2-4.

The catheter tip 802 may be a tip of a balloon catheter, having a balloon 804 at a terminal end of the catheter tip 802. The balloon 804 may be a compartment formed of a thin, flexible material, inflatable material, such as polyester, polyurethane, silicone, etc. The balloon 804 may be used to increase a size of a region in which the catheter tip 802 is deployed by inflating the balloon 804.

Figure 8A:
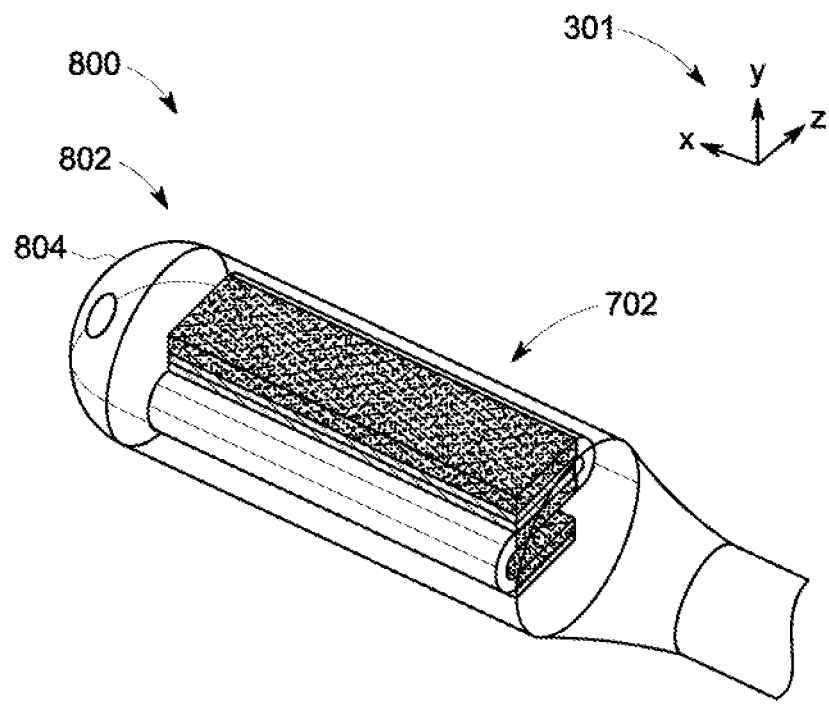
FIG. 8A shows a perspective view of the second example of the transducer of FIGS. 7A-7C in the folded configuration and enclosed in a balloon.
Figure 8B:
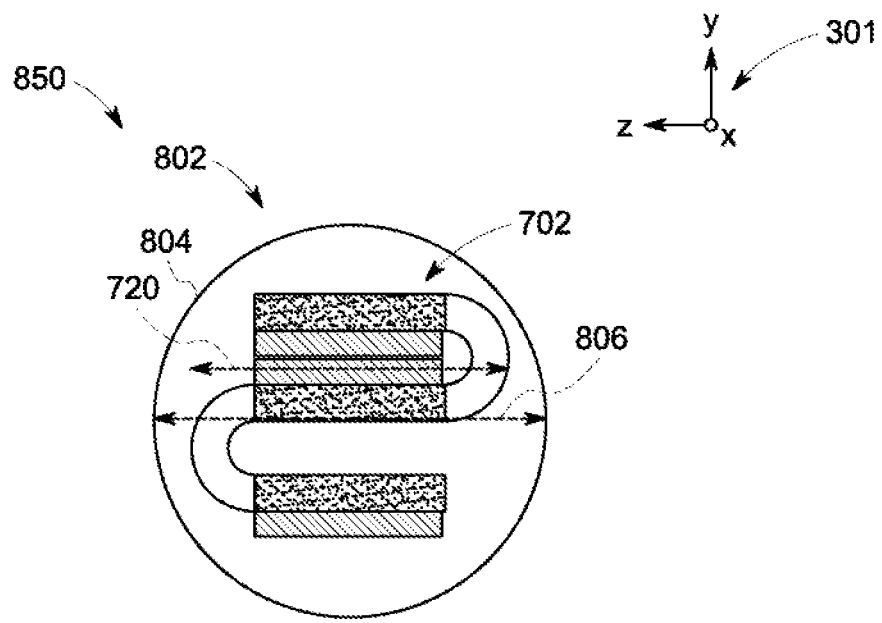
FIG. 8B shows an end view of the second example of the transducer in the folded configuration and enclosed in the balloon.

The transducer 702 is placed entirely inside of the balloon 804. In FIGS. 8A-8B, the balloon 804 is not inflated and the transducer 702 is in the first, folded configuration (e.g., as shown in FIGS. 7A and 7C). The balloon 804 may be substantially cylindrical, as shown in FIG. 8A, with an inner diameter 806 that is wider than the width 720 of the folded transducer 702, as shown in FIG. 8B.

Figure 9A:
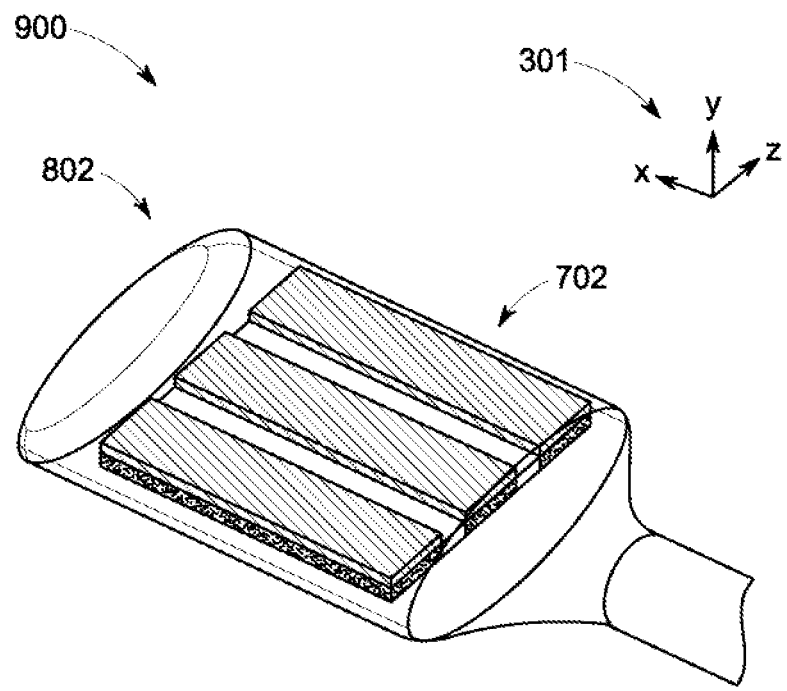
FIG. 9A shows a perspective view of the second example of the transducer of FIGS. 7A-7C in the unfolded configuration and enclosed in the balloon.
Figure 9B:
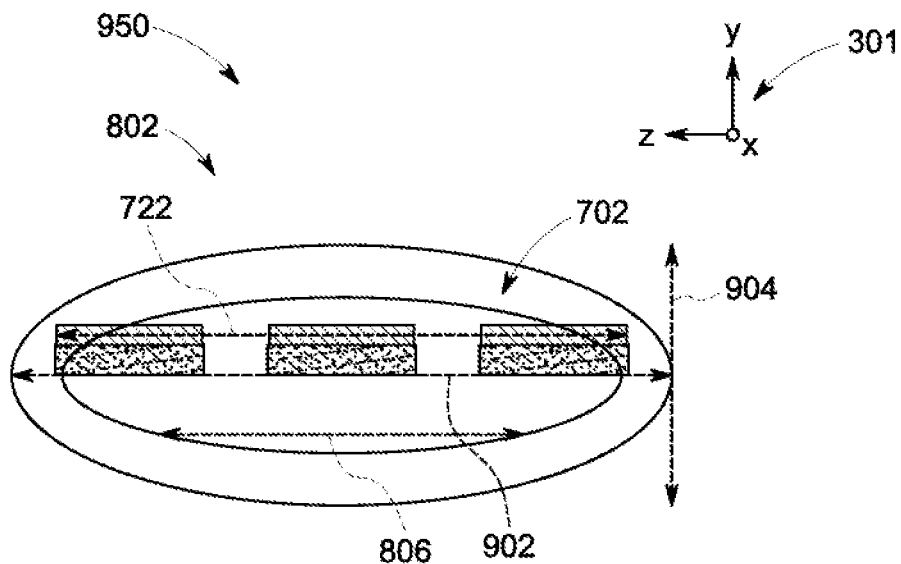
FIG. 9B shows an end view of the second example of the transducer in the unfolded configuration and enclosed in the balloon.

The balloon 804 may be inflated, as shown in a perspective view 900 in FIG. 9A and an end view 950 in FIG. 9B of the catheter tip 802. When inflated, the balloon 804 may be configured to expand mostly along one axis, such as the along the z-axis, resulting in an elliptical geometry of balloon 804 when viewed along the x-axis, as shown in FIG. 9B. For example, a width 902 of the balloon 804 may be greater than the diameter 806 of the balloon 804 when the balloon 804 is not inflated while a height 904 of the balloon 804 may become smaller than or remain similar to the diameter 806 of the balloon 804 when the balloon is not inflated.

The balloon 804 may be inflated by adding a fluid to the balloon 804. For example, a liquid, such as water or a saline solution may be added to the balloon 804 to increase a volume of the balloon 804 to a target volume that accommodates a size of the transducer 702 when the transducer 702 is unfolded, as shown in FIGS. 9A and 9B. In other examples, a gas may be used to expand the balloon 804, such as air or nitrogen.

When the balloon 804 is inflated, the transducer 702 may be adjusted to the second, unfolded configuration and/or operated in a manner similar to embodiments described previously. The width 902 of the inflated balloon 804 may be wider than the width 722 of the unfolded transducer 702, allowing the transducer 702 to unfold without inhibition to obtain imaging data at a target site. The material of the balloon 804, as well as the fluid used to inflate the balloon 804, may be selected based on a lack of interference of the material and fluid on transmission of imaging signals between the transducer 702 and the target site. For example, when the transducer 702 is implemented in an ultrasound probe, the balloon material and fluid do not attenuate or absorb at ultrasonic frequencies.

As an example, when the transducer is in the first, folded configuration, as shown in FIGS. 8A and 8B, and enclosed in the uninflated balloon, the SMPs of the transducer may be in a first, permanent shape when the SMPs are two-way memory shape polymers. The transducer may remain in the first shape while under a first condition, such as temperature, humidity, pH, etc., until the catheter tip reaches the target site and the balloon is inflated.

Once inflated, the transducer may be exposed to a second condition which triggers a shape change of the SMPs to the second, unfolded configuration. The second conditions may be maintained until scanning and data acquisition by the transducer is complete. The transducer may then be subjected to the first condition to return the transducer to the first, folded configuration. The balloon may be deflated by draining/venting the balloon.

In the first configuration of the transducer, the narrower diameter of the catheter tip, compared to the second configuration, may allow the catheter tip to be readily inserted through narrow pathways in the patient's body. The active area may be expanded to increase a capability and data quality of the transducer when the catheter tip is deployed at the target site and the balloon is inflated. The catheter tip may then be withdrawn from the target site by inducing the transducer to convert to the first configuration and deflating the balloon.

The change in footprint of the active area of the transducer between the first and second configurations is enabled by the folding of the transducer. Folding of the transducer at regions between the transducer arrays allows a coupling of rigid ASICs to each transducer array to be maintained while varying the size of the active area. The folded configurations shown in FIGS. 5, 6A, 7A, 7C, and 8A-8B show a pivoting of at least one transducer array by 180 degrees relative to an adjacent, stationary transducer array. It will be appreciated that such a description is for illustrative purposes and in other examples, each transducer array or segment may be pivoted during transitioning between shapes. Furthermore, in other examples, the transducer array or segment may be pivoted through different ranges of angles. For example, at least one transducer array or segment may be pivoted 90 degrees, 120 degrees, or any angle between 0 to 360 degrees relative to the adjacent, stationary transducer array or segment.

In operation, referring to the exemplary embodiment of the system 10 of FIG. 1 and the transducer 502 of FIG. 5, though transducers with more than two (2) segments or arrays are also operable in similar manners, the transducer 502 is initially moved into the expanded configuration via the movement of the SMP 508 as operated in a manner similar to embodiments described previously, to place the arrays or segments 504,506 in the desired configuration with regard to one another. However, it is also contemplated that other motive mechanisms can be utilized in place of the SMP 508, such as systems such as suitable micro-machines or micro-gears or also simpler mechanical mechanisms like spring-loaded mechanism or a catheter motion-induced expansion mechanism, among others. Once positioned by the SMP 508 or other suitable mechanism 507, the individual transducer elements 512 in each array or segment 504,506 are activated by applying a voltage to the elements under control of the imaging system 20/processing unit 21, optionally under the direction of the user via the interface 24. The applied voltage causes the elements to vibrate and emit ultrasound signals towards the structure around the transducer 502 to be imaged. The ultrasound signal is reflected off of the structure being imaged and returns to the transducer elements. The vibration created in the transducer element by the contact of the return ultrasound signal with the transducer element is converted back into a voltage that sent to the imaging system 20/processing unit 21 for use in forming an ultrasound image.

With the arrays or segments 504,506 each being formed with multiple transducer elements thereon, in order to enable the ultrasound signals emitted and/or received by the transducer elements 512 to effectively be utilized to form ultrasound images, the ultrasound signals are processed within the imaging system 20/processing unit 21 using a beamforming technique to directionally focus the signals in order reduce interference and create signal data that forms a clear ultrasound image. The beamforming technique applies a signal delay to each transducer element 512 in order to synchronize the signals that are emitted and/or received by each transducer element to compensate for the differences in the distances of the individual elements 512 from the structures being imaged and/or to direct the signals in a particular direction from the segments, i.e., to focus the signals on the desired structures to be imaged. The delay signals operate to enable each signal emitted and/or received by the individual transducer elements 512 to be effectively combined by the imaging system 20/processing unit 21 to form the ultrasound image.

However, in certain situations, as a result of limitations in the movement of the SMP in the various embodiments described previously for the device 14, the segments or arrays 504,506 of the transducer 502 may not be accurately positioned in the desired final position. With particular reference to the embodiment of FIG. 5, when the motive mechanism 507 (FIG. 11), e.g., SMP 508 is stimulated or operated by the imaging system 20/processing unit 21/user interface 24, e.g., subjected to temperature $T_2$ to move the arrays or segments 504, 506 of the transducer 502 into the planar configuration, the final position of the segments 504,506 at the end of the movement of the SMP 508 may not be perfectly planar due to any number of factors, e.g., the stimulus (temperature $T_2$) was not applied to the SMP 508 for a sufficient period of time, one of the segments 504,506 contacted a portion of or material within the structure to be imaged that prevented further movement of the segment 504,506, etc. In this situation, when the transducer 502 is operated to emit and receive the ultrasound signals using the individual transducer elements 512 on the segments 504, 506, the beamforming operation employed for the transmission and/or reception of the ultrasound signals by the segments 504,506 has to correct for the difference in the actual position of the segments 504,506 from the expected position of the segments 504,506. To determine and apply these corrections, there are a number of different processes and/or structures that can be employed in the imaging system 20/processing unit 21.

Figure 10:
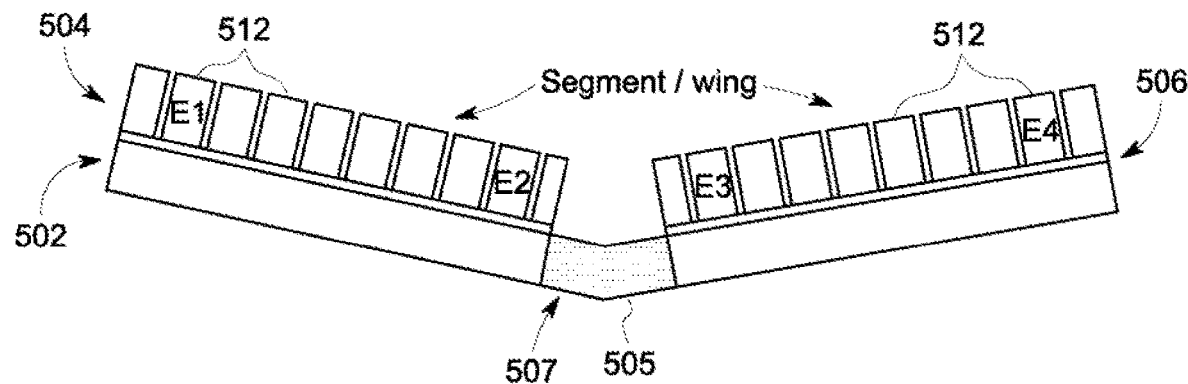
FIG. 10 is a schematic view of the deployable ultrasound imaging device transducer of FIG. 5 in a non-planar configuration.

Referring to FIG. 10, in one exemplary embodiment the correction process for the imaging system assumes that the individual transducer elements 512 have known and exact positions on each of the individual segments 504,506 that have been moved into the expanded position by the motive mechanism 507, e.g., the SMP 508. As the position of the individual transducer elements 512 on the separate segment 504,506 is known relative to one another (the segments 504,506 are each in a planar configuration across their entire width and length), the position uncertainty to be corrected is with respect to the relative positions of the segments 504, 506 with regard to each other. In this situation, conventional beamforming, e.g., delay and sum, Fourier based, etc., can be applied by the imaging system 20/processing unit 21 to both transmitted and received signals for those individual transducer elements 512 on each segment 504,506. The receive beamforming process applied to the elements 512 in each segment 504,506 can be accomplished with either unmodulated RF (radio frequency) or IQ (in-phase and quadrature) signals. Once the beamformed signals (or segment beamsums) for each segment 504,506 are created, these segment beamsums now need to be aligned with respect to each other to accommodate for any offset of the positions of the segments 504,506 relative to one another.

More specifically, in one exemplary embodiment of the disclosure the local beamsums for each segment 504,506 need to acoustically adjusted, i.e., time-aligned, by adding an offset to at least one the segment beamsums such that their sum adds constructively at the desired focal point. The necessary offset value or time shift can be estimated in several different ways, including, but not limited to the following processes employed within the imaging system 20/processing unit 21:

a) By correlation: correlating the segment beamsums against each other or against their sum before alignment and determining the time shift from the shift in the correlation function. The correlation function is defined as:

$$CC(\tau)=\int x(t)y(t+\tau)dt$$

where x and y are the segment beamsums. The time $\tau$ at which CC( ) is maximum is the time shift to be applied between the segment beamsums and also as the correction for the signal of subsequent transmit events for the segments.

b) The correlation can be simplified if the signal is assumed narrowband (valid assumption in many ultrasound imaging conditions). Now the time shift is equivalent to a phase shift at the center frequency. The phase shift can be determined as the phase of the complex product of one IQ signal with the conjugate of another IQ signal (or the IQ of the initial sum of the three segment IQ signals)

c) The time shift can also be determined iteratively (see G. Trahey, D. Zhao, J. A. Miglin and S. W. Smith, "Experimental results with a real-time adaptive ultrasonic imaging system for viewing through distorting media," in IEEE Transactions on Ultrasonics, Ferroelectrics, and Frequency Control, vol. 37, no. 5, pp. 418-427, September 1990, doi: 10.1109/58.105248, which is expressly incorporated herein by reference in its entirety for all purposes). In a first step the segment beamsums are added without a correction and the sum amplitude is recorded. Then a random time shift is applied and again the amplitude of the sum is recorded. If the amplitude of the second step is larger than the first then the shift of the second step is presumed to be more accurate than from the first step. Then again another random time shift is applied and the amplitude analysis is repeated until the amplitude approaches a steady state and cannot be further increased Once the positional offset, i.e., the phase or time shift, for the one or more segment beamsums are acoustically determined by the imaging system 20/processing unit 21, they are applied by the imaging system 20/processing unit 21 to the one or more segment beamsums before final summation into the overall beamsum and also to the subsequent transmit events for the segment beamsums. It should be noted that this exemplary embodiment of the process for acoustically determining the positional offset for the segment/segment beamsum centered on a single beamsum focused onto a single focus line. Most modern beamformers process multiple focus lines in parallel, also termed multiline acquisition (MLA). The time or phase delay estimation described above can be applied to the multiple focus lines either independently, i.e., the same algorithm applied by the imaging system 20/processing unit 21 to each of the MLAs, or in a coordinated manner where an assumption is made that the positional offset, i.e., time shifts, are the same among the MLAs and are determined only for one MLA but applied to all of them. Further, interpolation is feasible where the time delays are determined for a subset of the MLAs and interpolated delays are applied to the other MLAs.

In addition, while the acoustically determined positional offsets, or time or phase shifts are typically determined from signals received by the elements 512, those shifts can also be applied on subsequent transmit events/emitted ultrasound signals from the elements 512 to improve the transmit focusing. It has been shown that improved transmit focusing further improves the time shift estimation in the later receive events and thus the method becomes an iterative shift estimation over multiple transmit/receive events.

Figure 11:
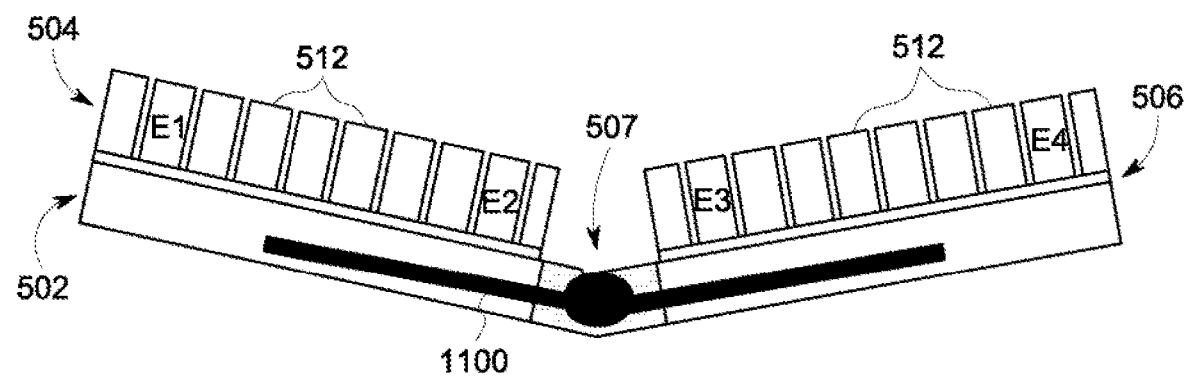
FIG. 11 is a schematic view of a second exemplary embodiment of the deployable ultrasound imaging device transducer of FIG. 10.
Figure 12:
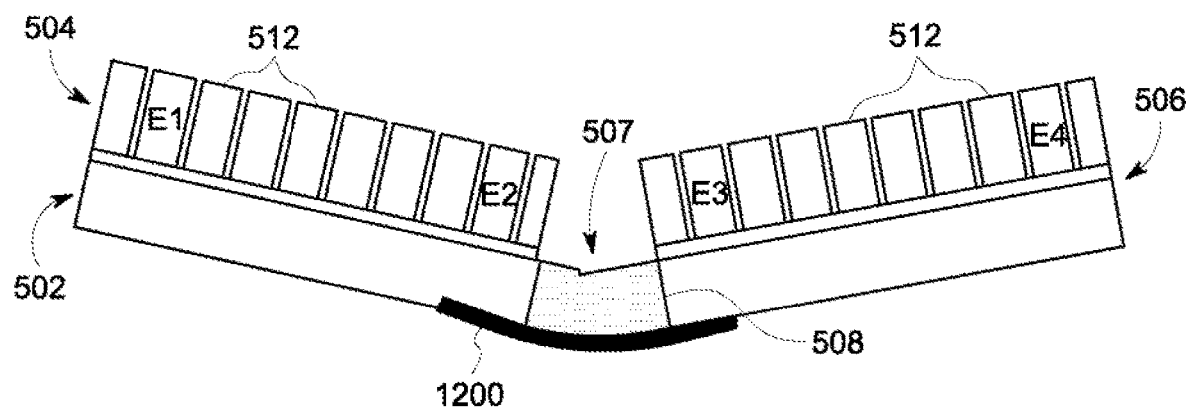
FIG. 12 is a schematic view of a third exemplary embodiment of the deployable ultrasound imaging device transducer of FIG. 10.
Figure 13:
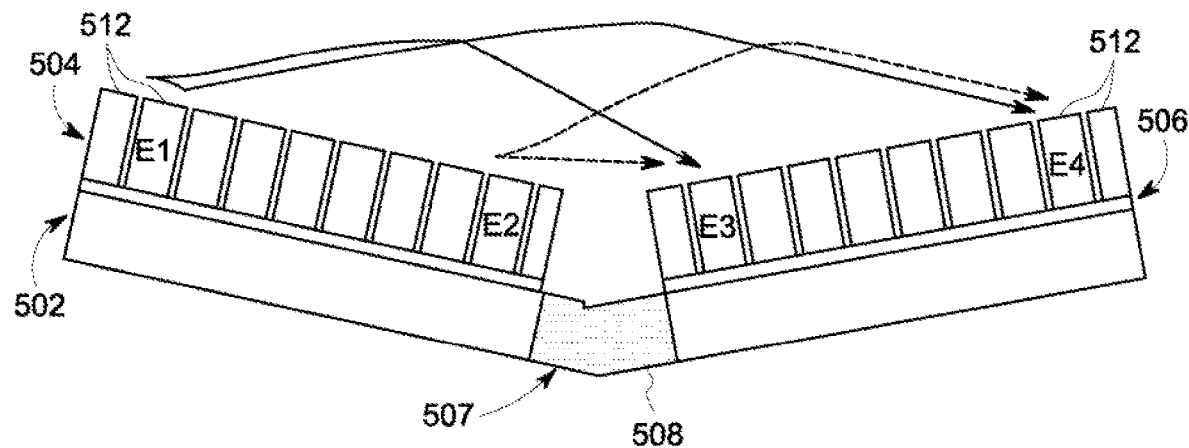
FIG. 13 is a schematic view of an exemplary embodiment of a time of flight measurement signal transmission for the deployable ultrasound imaging device transducer of FIG. 10.

The previous exemplary embodiments in which the positional offsets are determined by the acoustical measurement and/or analysis of the segment beamsums in the imaging system 20/processing unit 21 to determine the required time or phase shifts constituting the offset value(s) assumed that the mechanical inaccuracy of the positions of the individual segments 504,506 are small enough such that the ultrasound signals/beamsums from the respective segments 504,506 generally point in the same direction but have small time shifts with respect to each other. However, in the situation where the mechanical misalignment of the individual segments 504,506 is larger such that the ultrasound signals/beamsums or MLAs from each segment 504,506 point in different directions, then a positional offset value constituting a simple time or phase shift applied to the segment beamsum(s) might not be sufficient to correct for the misalignment between the segments 504,506. In this situation the beamsums from one or more of the segments 504,506 need to be steered in different directions before final summation, with steering corrections similarly applied to MLAs in the manner described previously, and optionally in addition to an acoustic determination of a positional offset described previously. In an exemplary embodiment of the disclosure, the process for the determination and application of the positional offset by the imaging system 20/processing unit 21 in the manner of a steering correction can be mechanical or acoustical in nature and include, but are not limited to, the following:

a) as shown in FIG. 11, using the attachment of an angular encoder 1100 on the transducer 502 and operably connected to the imaging system 20/processing unit 21 that tracks the actual opening of the segments 504,506;

b) as shown in FIG. 12, using the placement of a strain gauge or sensor 1200 between the segments 504,506 and along the SMP 508 or motive mechanism 507 across the mechanical bend line and operably connected to the imaging system 20/processing unit 21 to measure the deflection or angle between the segments 504,506, where the strain sensor 1200 can be positioned on either side of the transducer 502 or embedded within the bend structure 507,508 while not positioned at the neutral line of the strain;

c) performing an iterative optimization process in the imaging system 20/processing unit 21 to find the steering correction using either a gradient or global optimization, such as are well known in the relevant literature, where the optimization searches over the steering correction to find the maximum amplitude of the summed segment beamsums;

d) performing a correlation analysis (RF or IQ) in the imaging system 20/processing unit 21 similar to that described previously but using transducer element pairs from different segments 504,506. As shown in FIG. 13, by selecting four elements 512, with two elements 512 positioned close to one another (E2,E3) and two elements 512 positioned far apart from one another (E1, E4). The unknown angle between the two segments 504,506 can be determined by cross correlating signals <E1,E3> <E1,E4> <E2,E3> <E2,E4> or a subset thereof. This results in equivalent distances. These distances are used to solve the geometric problem of the wing angle and distance. The cross correlation CC=<x,y> being defined as:

$$CC(\tau)=\int x(t)y(t+\tau)dt$$

The time $\tau$ at which $CC(\tau)$ is maximum would be the time difference between the propagation times from a focal point within the reflecting tissue to the receiving element pairs e.g. E1 and E3. The time difference estimate can be made more accurate by bandpass filtering the received signal or averaging over multiple focal points; or e) employing a direct time measurement of the time required for an ultrasound signal to travel between an element of one wing to an element of the other wing as determined by the imaging system 20/processing unit 21. More specifically, one element 512 on segment 504 transmits an ultrasound pulse while the other element 512 on the segment 506 receives that pulse and determines the propagation time. With knowledge of the propagation speed of the signal through the transmission environment, e.g., tissue, bloodstream, etc., the distance between the transmitting and receiving element can be calculated. Again performing this measurement over multiple transmit/receive pairs of elements 512 allows for the improvement in the calculation of the angle and distance between the segments 504,506.

All of the aforementioned optimization algorithms for the determination of positional offsets and/or steering corrections stored within and utilized by the imaging system 20/processing unit 21 have better performance if the angle and distance between the segments is approximately known at the start of the optimization. This information typically comes from the design of the mechanical structure of the transducer 502. For example, if the angle between the segments 504,506 in the expanded or deployed position for the transducer 502 is designed to be 150° but in actual use is 160° due to one or more of the considerations discussed previously, then utilizing the nominal 150° angle value as the starting point for the optimization algorithm results in a faster and more consistent convergence of the optimization to the positional offset/steering correction value.

In addition to the position estimation described above for the determination of the positional offset and/or steering correction or offset values to be used, some of the methods or processes described previously also allow the simultaneous estimation by the imaging system 20/processing unit 21 of the speed of sound or attenuation of the acoustic propagation medium. For example, the four time of flight measurements between pairs of elements 512<E1,E3> <E1,E4> <E2,E3> <E2,E4> that were employed for the determination of the angle between the segments 504,506 to be used in determining the positional offset and/or steering correction or offset values contain redundant information about the segment position or angle. With these time of flight measurements, the remaining degrees of freedom can be utilized to calculate the speed of sound/attenuation of the ultrasound signals in the medium through which the ultrasound signals are transmitted, and thus provide additional information concerning the type and/or form of the medium.

Figure 14:
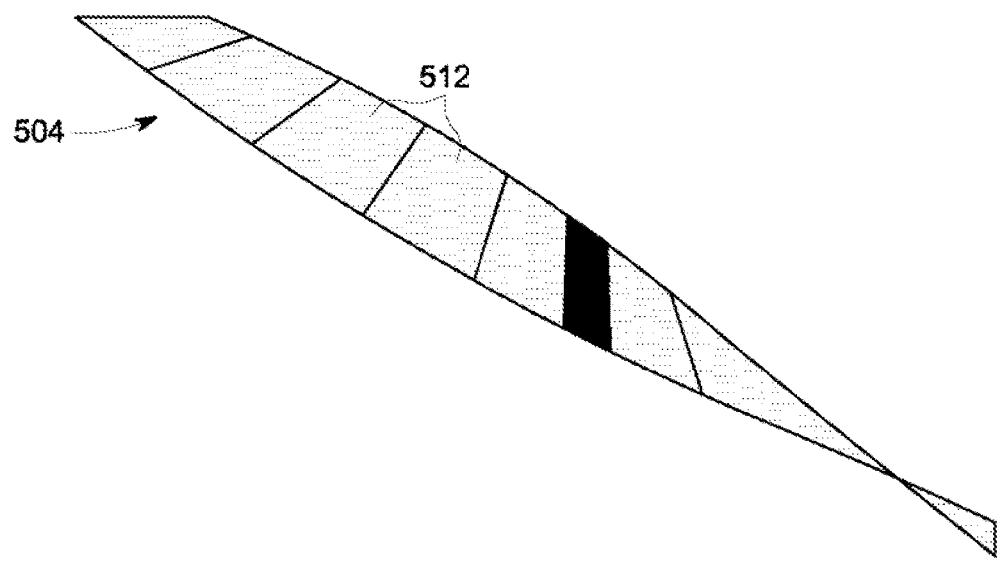
FIG. 14 is an isometric view of a distorted segment of the deployable ultrasound imaging device transducer of FIG. 10.

Due to the thin and potentially mechanically weak support structure forming each of the segments 504,506 of the transducer 502 described previously, it is additionally possible that one or more of the individual elements 512 within a segment 504,506 are not at their predetermined and/or assumed location with regard to one another. For example, a segment 504 that is designed with a flat profile could become deflected, twisted or otherwise distorted or warped when moved into the expanded or deployed position, as shown in FIG. 14. As described previously, nominal beamforming processes operate with the assumption that each of the individual transducer elements 512 are on the nominal flat plane of the segment 504,506, with the only positional differences being of the location of the particular element 512 on the planar segment 504,506 relative to the other elements 512. When the segment 504,506 is warped, such as due to the twisting of the segment 504,506 as a result of contact with a structure of fluid within the tissue being imaged, the discrepancy in the assumption of the location of the elements 512 causes beamforming errors which result in degraded image contrast mostly from increased beam sidelobes.

To address and mitigate this situation, a beamforming correction that accounts for the true element locations is determined by the imaging system 20/processing unit 21 and applied to the ultrasound signals. To determine the proper correction, a correlation, iterative or other correction algorithm similar to those described previously can be employed by the imaging system 20/processing unit 21 to find the relative positions of elements 512 within a deformed segment 504,506. Estimating the locations of the elements 512 using the algorithms can be done for all elements 512 on the segment 504,506 or for a subset of the elements 512. If only a subset is used, the other locations for the remaining elements 512 can be interpolated. Processing only a subset reduces the computational load and thus the time required, and interpolation is feasible because the shape change within the segment 504,506 is not erratic but smooth over the length and/or width of the segment 504,506. Further, the degree of interpolation that is feasible is dependent upon the smoothness of the segment 504,506 when warped, and therefore upon the sturdiness of the mechanical support structure for the segment 504,506.

In addition to the ability of the aforementioned correlating, iterative and other algorithms to provide position and/or steering offsets for use by the imaging system 20 in creating ultrasound images, the correction processes utilizing these algorithms can be utilized by the imaging system 20/processing unit 21 to track the movement/position of the segments 504,506 with respect to each other. This tracking can be performed at different points in time, in manners described as follows:

a) During segment movement to expanded position. Starting to track movement of the segments 504,506 using the correction algorithms, such as the time of flight calculation, while the segments 504,506 are still in the collapsed/undeployed position and continuing track movement of the segments 504,506 during the mechanical expansion provides information about the expansion process. For example, if the expansion is slower than designed for, the force that causes the expansion as applied under the direction of the imaging system 20/processing unit 21/user interface 24 can be increased. Similarly, if the expansion is too fast, the force can be reduced.

b) At the end of segment movement to expanded position: Enables confirmation that the expansion position is correct as well as providing beamforming corrections for any smaller position deviations as described previously.

c) Continued tracking of the position of the segments during imaging: Enables continuous correction of beamforming in one or more of the processes as described above in case the relative segment positions or segment shape/distortion changes over time, where the position/shape changes can be caused by various factors such as respiratory, muscular contraction and/or hemodynamic forces.

Tracking the relative positions of the segments 504,506 during movement also allows the system 20/processing unit 21 to stop the expansion at a predefined location, potentially prior to reaching the fully expanded position, performing an imaging procedure at that location, followed by repositioning of the segments 504,506 and imaging again. This process can be repeated as necessary.

Obtaining or performing a time of flight measurement while the segments 504,506 of the transducer 502 are in the collapsed position has a special implication with regard to later determinations of positional and steering offsets for the segments 504,506. In the collapsed position, each of the transducer element 512 and segment 504,506 positions are known with higher accuracy due to the lack of any errors created during movement of the segments 504,506 with regard to one another. The time of flight measurement then allows the system 20/processing unit 21 to determine the propagation speed of the ultrasound signals between the segments 504,506. Further, tracking using time of flight measurements at the end of the clinical procedure when the segments 504,506 are moved to the collapsed position can be compared with the time of flight measurement from the starting undeployed condition to enable confirmation that the segments/wings 504,506 have been correctly placed in the collapsed position before the device/catheter 14 is retracted or removed.

In addition, or as an alternative to the prior correction methods in which the beamsums are coherently summed in the process for determining a position or steering offset value, the segment beamsums can also be added incoherently by the imaging system 20/processing unit 21. The coherent summation described in the previous sections sums the RF or IQ data such that the phase information of the signals is retained. Thus, if two signals of equal amplitude and frequency but with 180 degree phase shift are added, their sum is zero. That is, signals can add constructively or destructively. With incoherent beamforming the segment signals are first magnitude detected or power detected by the system 20 and then added. Because the detected signals are always positive, i.e., any detectable signal has a positive magnitude or power value, they can only add constructively. This process has the advantage that phase or delay errors from incorrect positions of the transducer element(s) 512 and/or segments 504,506 or other wave propagation effects cannot create destructive interference. The disadvantage of the incoherent summation is that less resolution improvement from the expanded aperture provided by the expandable transducer segments 504,506 is achievable.

Coherent and incoherent summation can also be combined by the imaging system 20/processing unit 21. For example, if segment 504 has segment signals a and b, the coherent sum: $CS=a+b$ and the incoherent sum: $IS=|a|+|b|$. To combine the sums to arrive at the beamsum for the segment 504, and combine the higher resolution coherent signal data with the lower interference incoherent signal data, the following combination can be performed by the system 20:

$$\text{Combined sum:} CS+IS=a+b+|a|+|b|$$

$|a|$ denotes magnitude of a where a is a time signal. The magnitude $|a|$ can be determined by e.g. taking the absolute value of the signal a or taking the absolute value of the Hilbert transform (analytical signal) of signal a. Other related methods exist, e.g. using a lowpass filter in addition to taking the absolute value. This combined beamsum can then be utilized by the imaging system 20/processing unit 21 in any of the correction processes discussed previously for determining the positional and/or steering offset values for the individual segments 504. Further, in order to accommodate other considerations regarding the beamsum from a particular segment 504,506 formed in this combined manner, one or more weighting factors can be given to the incoherent and/or coherent signals.

Image and beam formation can be further improved in the system 20 employing the transducer 502 by the imaging system 20/processing unit 21 processing the signals from each segment 504,506 differently. For example, the transmit waveforms in different segments 504,506 can have different pulse lengths or different frequencies among other distinguishing signal characteristics. Similarly, the receive processing by the imaging system 20/processing unit 21 can apply different filters, e.g., bandpass or lowpass, or nonlinear processing to the signals from separate segments 504,506. For example, in certain situations it might be desirable to operate the center segment 504 at a higher frequency than the outer segment(s) 506.

Figure 15:
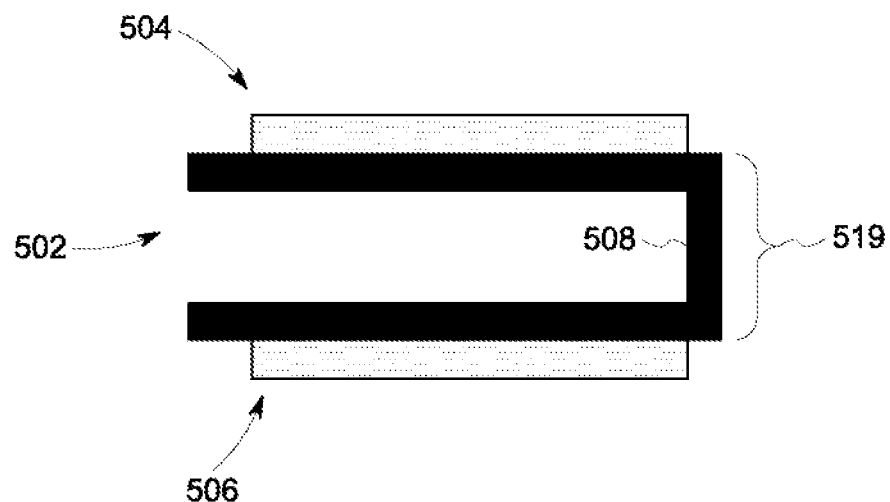
FIG. 15 is a schematic view of the deployable ultrasound imaging device transducer of FIG. 10 in a collapsed position.

According to another aspect of the present disclosure, conventional ultrasound produces images in the front of the transducer over a certain range of angles. The angles depend the pitch and imaging frequency of the individual elements on the transducer. For phase array transducers, typically +/−45 degree are achievable. With the construction of separate and moveable imaging segments 504,506 in the present disclosure, in their collapsed position shown in FIG. 15, it is possible to image from both segments 504,506 facing in opposite directions, such that the transducer 502 including these segments 504,506 can produce an image on both sides of the transducer 502. With this capacity, it is possible to achieve a close to spherical image or view of the structure around the transducer 502. Each of the top segment 504 and bottom segment 506 can image an approximate 3D half space around the transducer 502, i.e., the top segment 504, the upper half and the bottom segment 506, the lower half. As for a truly full spherical volume each segment 504,506 needs to be able to image a complete half volume around the transducer 502, practically this is not possible with two segment 504,506 as the segments 504,506 cannot image exactly parallel to their surfaces, such that a blind spot or gap 519 in the available image space exists. The size of this gap 519 can be minimized by employing a transducer 502 having more than two segments, such as, for example, a transducer with three segments arranged in a cross sectional triangular shape or four segments arranged in a cross sectional rectangular shape, among other possible configurations for the transducer.

Figure 16:
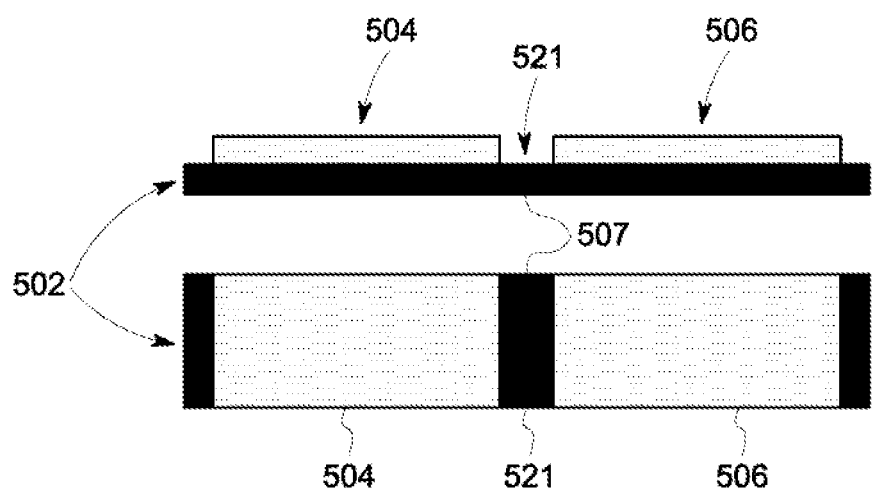
FIG. 16 is a schematic view of the deployable ultrasound imaging device transducer of FIG. 10 in an extended position.

In addition, when the transducer segments 504,506 expand from the collapsed position into the deployed or expanded position as shown in FIG. 16, the resulting imaging aperture formed by the segments 504,506 has element gaps 521 due to the space needed for the mechanical components for the motive mechanism 507 that facilitate the movement of the segments 504,506 in the transducer 502, e.g. the SMP 508 or other mechanical support and/or motive material(s).

Because a continuous imaging aperture without any gaps in the transducer element distribution creates beams with lower sidelobes and hence images with higher contrast, and because the mechanical structures 507 in the transducer 502 make some gaps 521 unavoidable, a number of processes can be employed by the imaging system 20/processing unit 21 to minimize the effects of the gaps 521 and improve the image quality.

Figure 17:
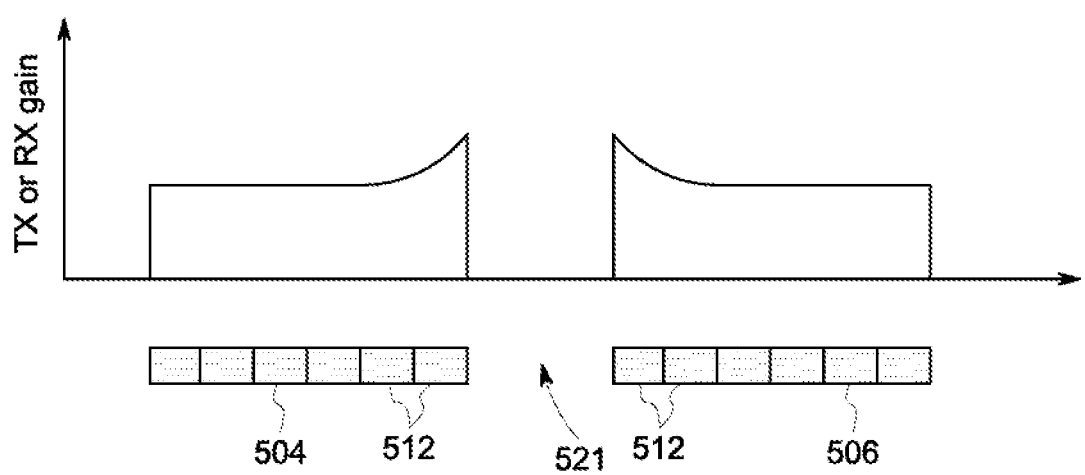
FIG. 17 is a graph of signal gains applied to transducer elements adjacent a gap of the deployable ultrasound imaging device transducer of FIG. 10.

A first process that can be employed by the imaging system 20/processing unit 21 is to compensate for the presence of the gaps 521 is giving higher weight to signals transmitted and/or received from those transducer elements 512 located on opposite sides of the gap 521, as schematically shown in FIG. 17. As the transducer elements 512 that are missing as a result of the gap 521 create a lack of signal from the location of the gap 521, by increasing the transmit pressure and/or the receive gain of the signals from transducer elements 512 adjacent the gap 521, the weighted signals compensate for lack of signals from the missing elements. Further, the increased weights applied to the transducer elements 512 on either side of the gap 521 do not have to be symmetrical.

Figure 18:
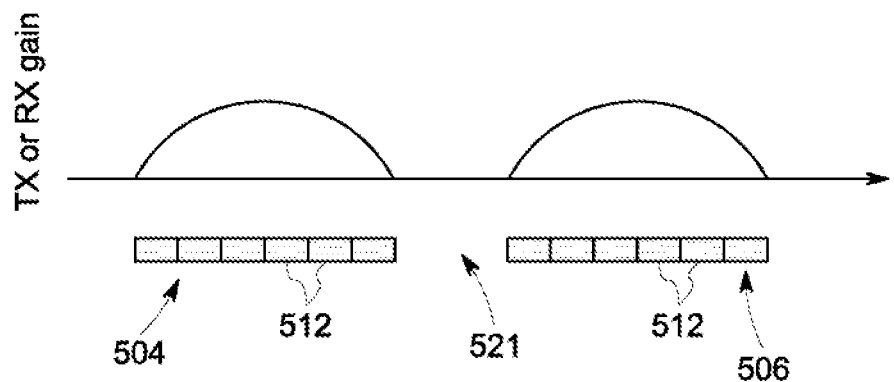
FIG. 18 is a graph of signal apodization applied to transducer elements of the deployable ultrasound imaging device transducer of FIG. 10.

As an alternative to increasing the weights of the signals from the transducer elements 512 on each side of the gap 521, the imaging system 20/processing unit 21 can apply a smooth apodization to the signals across all of the transducer elements 512 of each segment 504,506 to reduce the impact of the missing elements from the gap 521, as schematically illustrated in FIG. 18. More specifically, if the apodization applied to the signals for the transducer elements 512 by the imaging system 20/processing unit 21 approaches a signal strength of zero at the edge of the gap 521, the removal of any sharp transition in the signals from elements 512 adjacent the gap 521 limits the degradation of the ultrasound beam shape.

Figure 19:
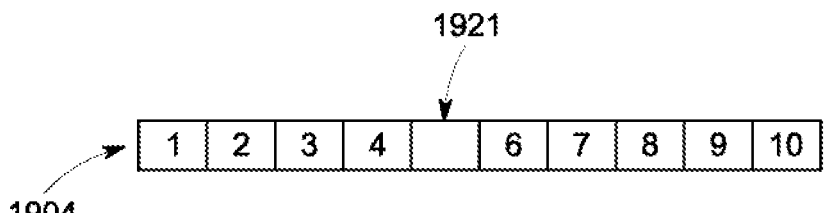
FIG. 19 is schematic representation of a first exemplary embodiment of an interpolation process for accommodating the gap in the deployable ultrasound imaging device transducer of FIG. 10.

In still another alternative process for minimizing the effects of the gap(s) 521 on image contrast/quality, the imaging system 20/processing unit 21 can provide an interpolated signal for the transducer elements 512 missing in the transducer 502 as a result of the presence of the gap 521. In the segments 504,506 the transducer elements 512 are equidistantly spaced along the segments 504,506. As schematically illustrated in FIG. 19, in an exemplary imaging aperture/segment 1904 with ten (10) transducer elements and channels, the n-th element provides signal s_n(t) to the n-th channel. In the situation where transducer element '5' is not present because of the gap 1921 this element provides no signal, s_5(t)=0, as input to the imaging system 20. To accommodate for this input signal deficiency, the imaging system 20/processing unit 21 can interpolate the missing signal as:

$$s\_n\_\text{estimated}(t) = (s\_(n-1)(t) + s\_(n+1)(t))/2$$

which in the present example becomes:

$$s\_5\_\text{estimated}(t) = (s\_4(t) + s\_6(t))/2$$

and provide the estimated signal "s_5_estimated (t)" to channel 5 of the imaging system 20 for use in forming the ultrasound image.

Further modifications and improvements to the missing signals can be made by a process for the imaging system 20/processing unit 21 employing more complex interpolation, such as the of spline interpolation, for example, at the expense of higher signal processing or computational loads. This exemplary process involves estimating the missing element signal from two or more neighboring elements, as represented by:

$$s\_n\_\text{estimated}(t) = (s\_(n-2)(t) + s\_(n-1)(t) + s\_(n+1)(t) + s\_(n+2)(t))/4$$

which in the case where the missing element is element 5 becomes:

$$s\_5\_\text{estimated}(t) = (s\_(3)(t) + s\_(4)(t) + s\_(6)(t) + s\_(7)(t))/4$$

where the imaging system 20/processing unit 21 utilizes signals 3 and 4 on one side and 6 and 7 on the other side for the interpolation. Also, different weights can be provided to the signals uses, such that in the above example, the signals for elements 4 and 6 can be weighted higher than the signals for elements 3 and 7.

Figure 20:
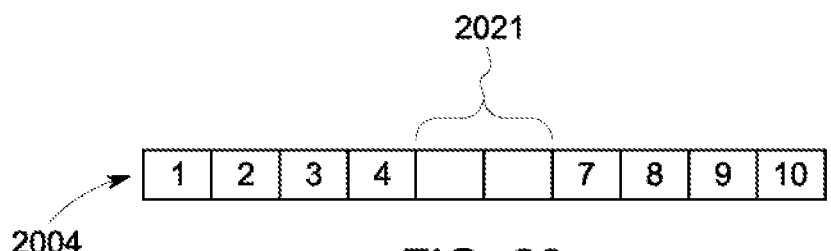
FIG. 20 is schematic representation of a second exemplary embodiment of an interpolation process for accommodating the gap in the deployable ultrasound imaging device transducer of FIG. 10.

If the gap 2021, as schematically illustrated in FIG. 20, is larger than one element, then multi-element interpolation can be performed by the imaging system 20/processing unit 21. For example, if elements 5 and 6 are missing due to the presence of the gap 2021 in exemplary segment 2004, then the interpolation for each missing element is carried out as:

$$s\_5\_estimated(t)=2/3*s\_4(t)+1/3*s\_7(t)$$

$$s\_6\_estimated(t)=1/3*s\_4(t)+2/3*s\_7(t)$$

where the elements closer to the missing element are provided with a higher weight than those spaced further from the missing element.

Figure 21:
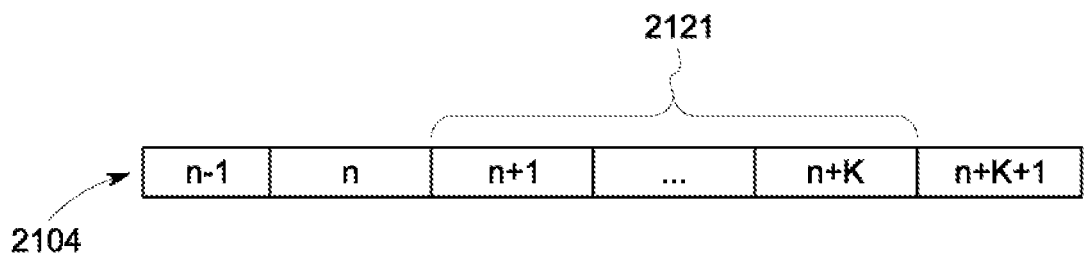
FIG. 21 is schematic representation of a third exemplary embodiment of an interpolation process for accommodating the gap in the deployable ultrasound imaging device transducer of FIG. 10.

Signals for elements missing as a result of even larger gaps 2121 in a segment 2104 as shown in FIG. 21 are estimated by the imaging system 20/processing unit 21 extending the linear interpolation described previously regarding FIG. 20. In extending this interpolation, the imaging system 20/processing unit 21 utilizes the last available element on the left of the gap 2121 as element 'n' followed by K non-existent elements forming the gap 2121 and terminating on the right end of the gap 2121 at the next available element at location 'n+K+1'. The interpolation for a signal from a missing element 'k' within the gap 2121, k=[1,K] employed by the imaging system 20 is as follows:

$$s\_n+k\_estimated(t)=(K+1-k)/(K+1)*s\_n(t)+k/(K+1)*s\_n+K+1(t)$$

In this manner, with regard to the gaps 521 formed in the transducer 502 between the segments 504,506, the imaging system 20/processing unit 21 can determine the number of elements 512 missing based upon the known size of the gap 521 and can interpolate signals for each of the missing elements utilizing signals from the elements 512 located on either side of the gap 521 using these processes to improve the ultrasound image quality/resolution from the transducer 502.

Another aspect of the present disclosure addresses the limitation of prior ultrasound imaging devices with regard to the number of signal connections that can be brought from the console/imaging system 20 to the imaging ASIC at the tip of the device due to limited cross-sectional area of the device. As the mechanically expandable transducer 502 disclosed herein typically has 2-5 times the number of transducer elements 512 compared to a prior art non-expanding transducer, a signal connection between the ASIC 318 (FIG. 3) and the imaging system 20/processing unit 21 along the cable 310 (FIG. 3) needs to be shared between two or more channels for the elements 512. In the present disclosure, channel means either literally an output signal from a transducer element 512 or a local beamsum created by the ASIC 318 for the transducer 502 or transducer segment 504,506. For example, the local ASIC 318 for a segment 504 might beamform a 5×5 patch of transducer elements 512 to form a local beamsum, which is referred to as sub-aperture processing. This local beamsum needs to be forwarded from the transducer 502 to the console/imaging system 20/processing unit 21 for final beamforming/signal processing to create the ultrasound image.

To facilitate the transmission of the signals between the transducer 502 and the imaging system/console 20/processing unit 21, the following are some concepts for sharing channels/transducer element output signals over the limited number of physical signal connections.

The first exemplary process of the present disclosure involves simultaneous channel multiplexing and can be applied to the transmission of two or more transducer element output signals or channels along a single physical connection. More specifically, as disclosed in U.S. Pat. No. 6,506,160, entitled Frequency Division Multiplexed Wireline Communication For Ultrasound Probe and which is hereby expressly incorporated by reference herein in its entirety for all purposes, simultaneous channel multiplexing can be employed by the imaging system 20/processing unit 21 in a situation where two example output signals/channels C1 and C2 need to be transported over a single physical signal connection have a maximum frequency content of $F_{max}$, where the channels C1 and C2 occupy the same frequency range as they are derived from similar ultrasound signals. With these parameters, the following are versions of simultaneous channel multiplexing of the transducer element output signals/channels that can be employed:

a) Time domain multiplexing: Both channels are broken up into time slices and alternatingly given access to the physical signal connection/cable/circuit 310. Then, by defining an access time length of $T<F_{max}/4$, channel C1 is transmitted during 2kT to (2k+1)T while channel C2 is transmitted during (2k+1)T to (2k+2)T, with this pattern being repeated to deliver all the data carried in the channels C1 and C2. A receiver (not shown) in the console/imaging system 20/processing unit 21 performs demultiplexing with the original, and optionally time-shifted set of access time slots and thereby recreates the original channels C1 and C2 for subsequent beamforming in the imaging system 20/processing unit 21.

b) Frequency domain multiplexing: Modulating channels C1 and C2 with different carrier frequencies separates their spectrum and the modulated channels can be added together and transmitted simultaneously over the same physical signal connection 310. The receiver in the console/imaging system 20/processing unit 21 performs demodulation with the original set of carrier frequencies and thereby recreates the original channels for subsequent beamforming. The frequency separation of the carriers should be at least $2*F_{max}$. It is also possible to leave one of the channels at baseband, i.e. not modulating one of the channels being transmitted.

c) Analog to Digital conversion and digital multiplexing: The channels C1 and C2 can be digitized with an analog-to-digital converter (ADC) and the digital bit stream can be multiplexed over the single signal connection 310. There are many methods of digital multiplexing. In addition to the time and frequency domain multiplexing that can also be applied to digital signals, code division multiplexing in various forms or phase shift modulation are common digital encoding schemes. The ADC can be implemented in a variety of ways, e.g. delta-sigma, flash, successive approximation and other common techniques.

The signals to be multiplexed can either be directly received element signals, element signals that have gone through an amplifier or subaperture processed signals. Subaperture Processing (SAP) refers to local beamforming of a subset of the total receive elements. For example, if a receive aperture has 100×100 elements (i.e. 10,000 elements) then 5×5 SAPs would create 400 5×5 subapertures. Each SAP beamforms 25 (5×5) elements into a single channel that needs to be transmitted to the imaging system. Thus, instead of sending 10,000 signals, only 400 need to be sent.

The above-described modulation or multiplexing techniques allow multiple channels to be transmitted over the same physical signal connection. In the ideal case, the receiver of the multiplexed channels (i.e. the console/imaging system 20) can separate the channels and process them independently. However due to nonideal effects, for example bandwidth limitations, nonlinear distortions, carrier clock phase shifts, etc. the demultiplexing creates some level of channel crosstalk. This crosstalk should be minimized, but to reduce the effects of any residual crosstalk the channels C1 and C2 should originate from sub-apertures of the segments 504,506 that are physically close to each other, and preferably adjacent one another. That way, the erroneous crosstalk affects are spatially limited and cause only limited beam degradation.

An alternative to simultaneous multiplexing for transmission of multiple channels/transducer element output signals over a single connection 310 between the elements 512 and the imaging system 20/processing unit 21 described above is synthetic aperture imaging, or non-simultaneous multiplexing. Again, in the case of two channels C1 and C2, which can represent individual transducer elements 512, or sub-apertures defined by sub-sets of the transducer elements 512 located on a segment 504, 506 of the transducer 502, two identical ultrasound transmit events are employed to separately receive C1 and C2. On the first transmit, channel C1 is acquired and sent from an aperture processor (not shown) to the console/imaging system 20/processing unit 21 and on the second transmit channel C2 is sent from an aperture processor to the console/imaging system 20/processing unit 21. Examples of the structure and method for performing the aperture/sub-aperture processing are disclosed in U.S. Pat. No. 7,775,982, entitled Method and System For Sub-Aperture Processing, the entirety of which is expressly incorporated herein by reference for all purposes. Beamforming of the channels C1 and C2 in the console/imaging system 20/processing unit 21 is completed once both channels have been acquired.

A drawback of this method is that the ultrasound image produced can suffer from motion artifacts since the signals from channels C1 and C2 are not acquired at the same time. If the imaging target has moved in-between the acquisitions, e.g. has moved towards the transducer, then C1 and C2 will have an undesired phase shift which degrades the final beam shape and image contrast and/or image resolution. To reduce this problem, motion estimation and compensation can be applied in the imaging system 20/processing unit 21 in which any motion of the target is estimated over multiple transmit events by tracking the phases of the reflection or by tracking the speckle in the resultant image. Once the motion is known, the imaging system 20/processing unit 21 can apply a phase correction or time shift between channels C1 and C2 to compensate for the motion induced shift, which can be determined according to any of the aforementioned corrections processes. Further, depending on what type of image degradation might be acceptable, the spatial distribution of the transducer elements on the segments forming C1 and C2 can be optimized. For example, if C1 and C2 are adjacent and followed by adjacent C3 and C4, the resulting image artifact will be a grating lobe; i.e. a spurious reception direction far from the target location. Alternatively, if C1 and C2 are on different transducer segments 504,506 then grating lobe is not a problem but regular sidelobes could increase, again degrading image contrast. In addition, as previously discussed, the use of incoherent summation of the synthetic aperture components avoids the phase cancellation problem.

According to another exemplary embodiment of the present disclosure, as an alternative solution to the previously described multiplexing transmission processes to address the fundamental problem of transmitting all transducer output signals/channels to the console/imaging system 20 as constrained by the limited cross sectional area of the device, an ultrasound device 14 can employ optical communication or fiber optic connections (not shown) in place of the cables 310 connecting the ASIC 318 and the imaging system 20/processing unit 21. A fiber optic connection has an information density 100× to 1000× higher than the typical electrical communication/wire used in prior art ultrasound systems/probes. Thus, replacing the electrical signal communication/wired connections between the ASIC 318 and the console/imaging system 20/processing unit 21 with fiber optic connections alleviates the problem of not having the physical space for the transmission of all transducer element output signals/channels in the device 14. To make this change, optical communication requires the ultrasound signal to be modulated onto an optical carrier signal and standard methods for this exist and can be done in conjunction with analog or digital signals, e.g. analog optical modulator such as those disclosed in U.S. Pat. No. 7,367, 945, entitled Ultrasound System, and U.S. Pat. No. 7,615, 009, entitled System and Method for Optical Data Transmission in Ultrasound Imaging, each of which are expressly incorporated by reference herein in their entirety for all purposes. Similarly, for a digital signal, the transducer element output signal/channel signal can be first converted into a digital signal and then the digital signal can be communicated over the fiber optic channel. Numerous well-known methods exist for analog to digital conversion and for digital optical communication.

In still another alternative embodiment of any of the aforementioned versions of the present disclosure, in certain cases the shape memory materials (SMM), e.g., SMP 508, are activated by heat (or temperature). As a result, a heat source (not shown) needs to be applied as the stimulus to the SMP 508 on order to activate and move the SMP 508 and expand the array segments 504,506 of the transducer 502. In certain embodiments, the heat source would be a dedicated heat source secured to the transducer 502 adjacent to or contained within the SMP 508 and controllable from the console/imaging system 20. In other alternative embodiments, as the ASIC on each segment 504,506 of the transducer 502 generates heat when in operation, the ASIC can be utilized as the heat source. With regard to the SMP 508, or other SMM, a temperature sensitive SSM requires exact control of the applied heat and temperature increase or decrease for proper operation of the SMM. The temperature of the SMM and its surroundings can be measured with a temperature sensor (not shown) integrated in the ASIC 318 or as a separate sensor, e.g. thermistor, integrated within the structure of the transducer 502.

In still another alternative embodiment, the SMM requires an electrical stimulus for movement where the stimulus activates the SMM via an electric field applied to the SMM or by creating heat from electric current. To simplify the manner and number of the connections between the transducer 502 and the console/imaging system 20/processing unit 21, the electrical stimulus for the SMM/SMP 508 is provided by the beamforming ASIC 318. The ASIC 318 already has high voltage capability as a result of its ultrasound transmit function. Control of the ASIC 318 to provide the stimulus is controlled by the console/imaging system 20/processing unit 21 (responding to user or AI commands), while the transfer of the command to the ASIC 318 is facilitated by the already existing control communication between the ASIC 318 and the console/imaging system 20/processing unit 21 by adding a specific digital command.

While various mechanisms for the movement of the transducer segments 504,506 relative to one another have been disclosed, the expansion and contraction of the imaging aperture/transducer segments 504,506 in one embodiment is initiated by the clinical user. For example, once the user has determined that the ultrasound device 14 is at the right location for the aperture segments 504,506 to be expanded, the user gives a command to the imaging system 20/processing device 21 to expand the segments 504,506, such as through the interface 24. Similarly, before retraction of the device 14, the user gives a command via the interface 24 to move the segments 504,506 into their folded or collapsed positions. Additionally, while the interface 24 can be configured to receive standard touch-screen, keyboard or mouse commands, the interface 24 can also be configured to receive voice commands interpreted by a voice detection module (not shown) or gestures interpreted by appropriate gesture detection software and hardware (not shown) included within the imaging system 20.

Alternatively, instead of user commands, the imaging system 20/processing unit 21 can incorporate an artificial intelligence (AI) block or engine (not shown) that can initiate the expansion/contraction of the segments 504,506 of the transducer 502 based on images available to the AI block from the imaging device 20/processing unit 21, or as a result of other information, such as information inferred from other user actions. For example, images obtained from the device 14 with the still collapsed transducer 502 may indicate the location of the transducer 502, i.e., that the transducer 502 is properly located for the desired images, e.g., is in the right atrium, and that the transducer 502 should be expanded. Further, when images from the device 14 indicate that the transducer 502 is being retracted from the desired location, or close to the retraction position, then the AI may initiate the collapse function for the transducer 502. Once the movement command is received, such as from the user or from the AI, the console/imaging system 20/processing unit 21 initiates the proper function, e.g. applying a heat or voltage stimulus to the SMM, to affect the expansion or contraction of the segments 504,506 of the transducer 502. Additionally, during the expansion or contraction movement, the console/imaging system 20/processing unit 21 can monitor the movement progress and adjust the stimulus as needed, e.g., to accelerate or slow down the motion of the SMM/SMP 508. The status of segment deployment of the segments 504,506 as determined by the imaging system 20/processing unit 21 can be shown to the user via an on-screen indication (not shown) on the display 22. This indication can have any suitable form to represent the status of the deployment of the expandable transducer 502, such as pictorial, i.e., showing an expanded or collapsed segment arrangement that can be two-state, i.e., either deployed or collapsed, or gradual, i.e., showing various intermediate stages of the deployment, including but not limited to a percentage number, i.e., 0% meaning fully collapsed and 100% meaning fully deployed, with other intermediate percentage values. This indication is desired as knowledge of the deployment status of the transducer 502 is critical to avoid patient injury during insertion or extraction or other movements of the ultrasound device 14 including the transducer 502. As a result, the imaging system 20/processing unit 21 can also be configured to provide warnings to the user when any movement of the device 14/transducer 502 is detected while the transducer 502 is not in the collapsed position to attempt to avoid injury to the patient from premature movement of the ultrasound device 14.

Figure 22A:
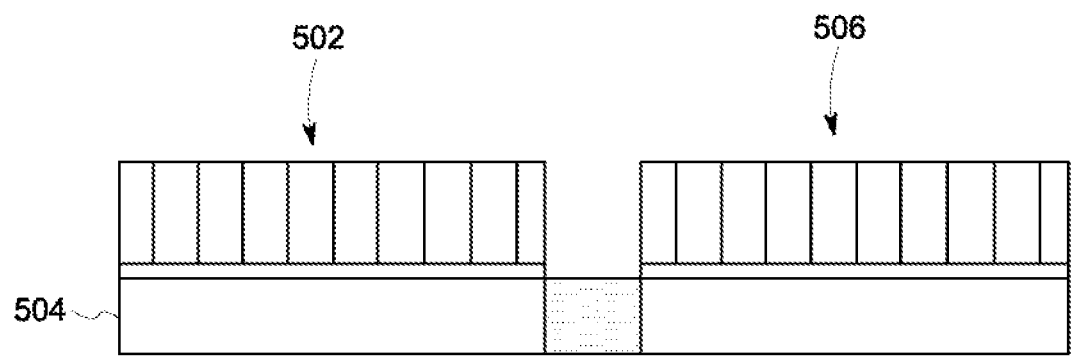
FIGS. 22A-C are schematic views of the deployable ultrasound imaging device transducer of FIG. 10 in planar, concave and convex operating configurations.
Figure 22B:
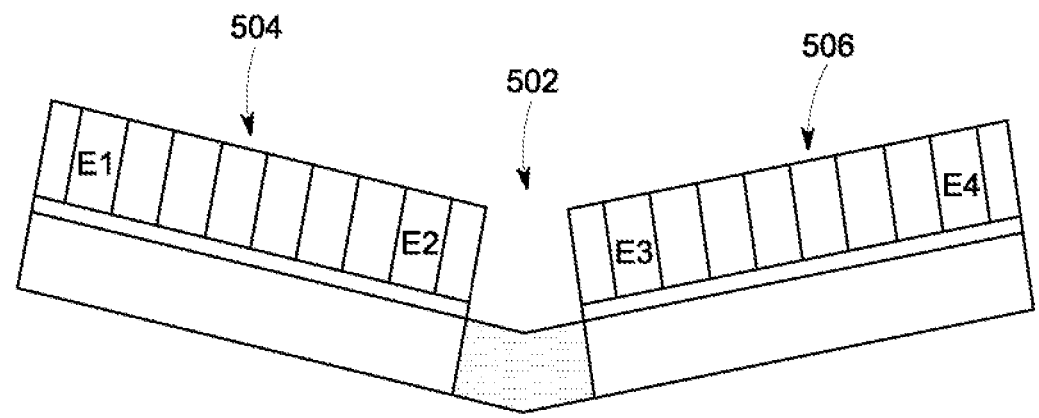
Figure 22C:
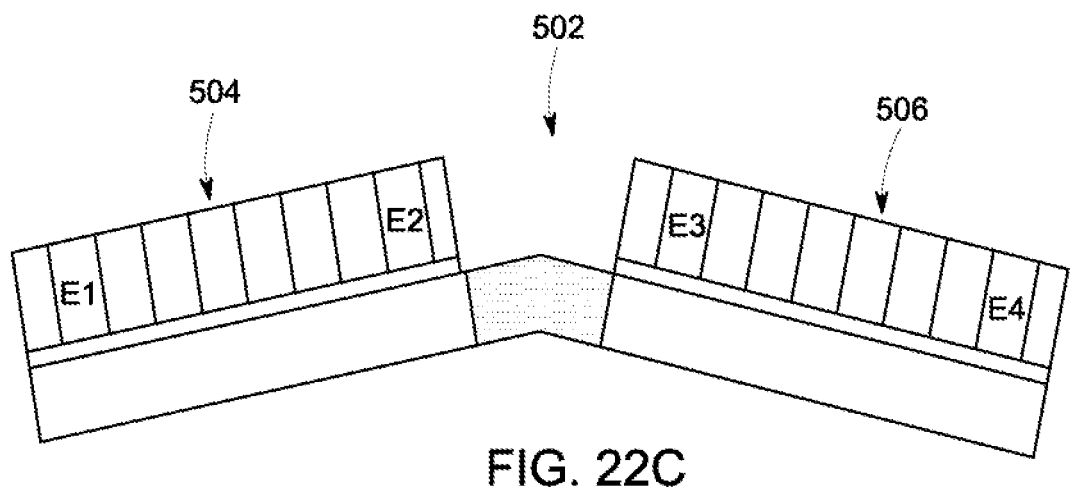

In another exemplary embodiment, while in prior embodiments it is desired to have the segments 504,506 of the transducer 502 in a flat, planar configuration A to maximize the imaging aperture provided by the segments 504,506, in a transducer 502 having two or more segments 504,506, in certain applications or procedures it can be desirable to position the segments 504,506 in a concave configuration B or convex configuration C, as shown in FIGS. 22A-C. More specifically, in addition to the imaging system 20/processing unit 21 having the ability to compensate for the non-planar positions of the segments 504,506 and for the gap 521 lacking any transducer elements 512 as describe previously, while the flat configuration A might be the most versatile, the concave configuration B has advantages when only a small area in front the transducer 502 needs to be imaged. The concave configuration B also has advantages if the segments 504 and/or 506 are operated to provide higher acoustic power to a tissue region for therapy purposes, such as for tissue heating or ablation. Further, the convex configuration C provides a wider field of view for any obtained ultrasound images, which for example is advantageous for tracking other devices, such as catheters. Additionally, separate from the positioning of the segments 504,506 in either a concave or convex position by the selective operation of the motive mechanism 507, e.g., the SMP 508, the individual segments 504,506 can themselves optionally be curved in either a convex or concave shape (not shown) to further improve certain image formation characteristics as energy focusing or enhanced field of view.

Figure 23:
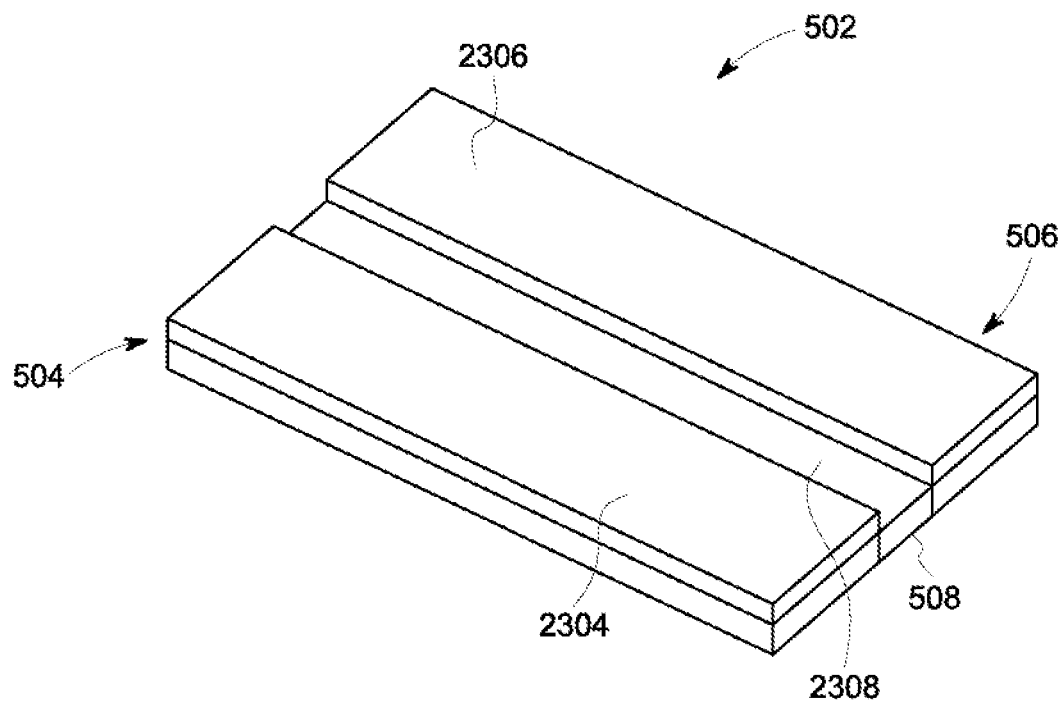
FIG. 23 is an isometric view of the deployable ultrasound imaging device transducer of FIG. 10 in a first continuous wave Doppler operating configuration.
Figure 24:
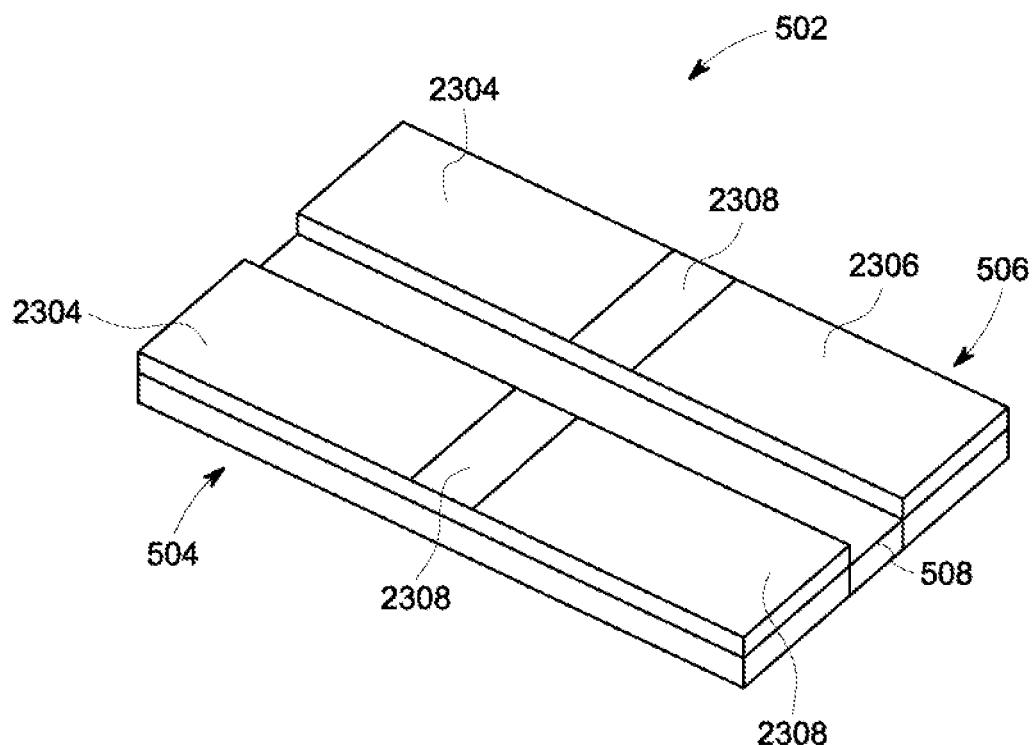
FIG. 24 is an isometric view of the deployable ultrasound imaging device transducer of FIG. 10 in a second continuous wave Doppler operating configuration.

In addition to the pulsed manner of operation of ultrasound devices 14 for the imaging of structures adjacent the devices 14, many ultrasound transducers 502, including those employed on ultrasound catheters and ultrasound endoscopes can be operated to provide a continuous wave (CW) Doppler imaging function/configuration. The operation of the transducer 502 in a CW manner requires dedicated transmit and receive areas on the overall imaging aperture formed by the transducer 502. Typically, there is also a smaller, inactive area between the transmit and receive areas, i.e. it neither transmits nor receives ultrasound signals to reduce the acoustic crosstalk between the transmit section/area and the receive section/area. Looking at FIG. 23, in the illustrated exemplary embodiment the imaging system 20/processing unit 21 and the transducer 502 can be configured for operation in a CW manner by utilizing one segment 504 as the transmit section 2304 and the other segment 506 as the receive section 2306, with the SMP 508 constituting the inactive area 2308. Alternatively, the transmit and receive separation can be done with a transmit section 2304 and a receive section 2306 on a single segment 504,506 separated by an inactive area 2308 of transducers 512, as shown in FIG. 24.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A method of determining relative position offsets for transducer segments of an ultrasound device including a number of relatively movable transducer segments, the method comprising the steps of:

a. providing an ultrasound device including a first transducer segment moveably connected to a second transducer segment via a controllable actuator;
b. moving the first transducer segment relative to the second transducer segment by operating the controllable actuator;
c. determining a positional offset for ultrasound signals emitted from the first transducer segment relative to ultrasound signals emitted from the second transducer segment; and
d. correcting subsequent ultrasound signals emitted from or received by at least one of the first and second transducer segments using the positional offset to produce an ultrasound image, wherein the step of determining the positional offset for the first transducer segment comprises determining the positional offset with an acoustic measurement of a number of ultrasound signals received by the first transducer segment and the second transducer segment, wherein the step of determining the positional offset with an acoustic measurement of a number of ultrasound signals received by the first transducer segment and the second transducer segment comprises the steps of:
a. obtaining a first set of ultrasound signals from the ultrasound signals received by the first transducer segment;
b. obtaining a second set of ultrasound signals from the ultrasound signals received by the second transducer segment; and
c. correlating the first set of ultrasound signals to the second set of ultrasound signals to determine the positional offset, and wherein the step of correlating the first set of ultrasound signals to the second set of ultrasound signals comprises the steps of:
a. converting each of the first set of ultrasound signals and the second set of ultrasound signals into an in-phase component and a quadrature component to form a first IQ signal and a second IQ signal;
b. multiplying one of the first or second IQ signals with the complex conjugate of the other of the first or second IQ signal to form a product;
c. determining the phase of the product;
d. using the phase to estimate the positional offset.

2. A method of determining relative position offsets for transducer segments of an ultrasound device including a number of relatively movable transducer segments, the method comprising the steps of:
a. providing an ultrasound device including a first transducer segment moveably connected to a second transducer segment via a controllable actuator;
b. moving the first transducer segment relative to the second transducer segment by operating the controllable actuator;
c. determining a positional offset for ultrasound signals emitted from the first transducer segment relative to ultrasound signals emitted from the second transducer segment; and
d. correcting subsequent ultrasound signals emitted from or received by at least one of the first and second transducer segments using the positional offset to produce an ultrasound image, wherein the step of determining the positional offset for the first transducer segment comprises determining the positional offset with an acoustic measurement of a number of ultrasound signals received by the first transducer segment and the second transducer segment, wherein the step of determining the positional offset with an acoustic measurement of a number of ultrasound signals received by the first transducer segment and the second transducer segment comprises the steps of:
a. obtaining a first set of ultrasound signals from the ultrasound signals received by the first transducer segment;
b. obtaining a second set of ultrasound signals from the ultrasound signals received by the second transducer segment; and
c. correlating the first set of ultrasound signals to the second set of ultrasound signals to determine the positional offset, and wherein the step of correcting the ultrasound signals comprises the steps of:
a. applying the determined positional offset to subsequent ultrasound signals received by the first transducer segment to form a first coherent ultrasound signal data set;
b. combining the first coherent ultrasound signal data set from the first transducer segment with a second coherent ultrasound signal data set from the second transducer segment to form a combined coherent ultrasound signal data set;
c. determining a first incoherent ultrasound signal data set from the first transducer segment;
d. determining a second incoherent ultrasound signal data set from the second transducer segment;
e. combining the first incoherent ultrasound signal data set with the second incoherent ultrasound signal data set to form a combined incoherent ultrasound signal data set; and
f. combining the combined coherent ultrasound signal data set and the combined incoherent ultrasound signal data set to form an ultrasound image.

3. A method of determining relative position offsets for transducer segments of an ultrasound device including a number of relatively movable transducer segments, the method comprising the steps of:
a. providing an ultrasound device including a first transducer segment moveably connected to a second transducer segment via a controllable actuator;
b. moving the first transducer segment relative to the second transducer segment by operating the controllable actuator;
c. determining a positional offset for ultrasound signals emitted from the first transducer segment relative to ultrasound signals emitted from the second transducer segment; and
d. correcting subsequent ultrasound signals emitted from or received by at least one of the first and second transducer segments using the positional offset to produce an ultrasound image, wherein the step of determining a positional offset for ultrasound signals emitted from the first transducer segment relative to ultrasound signals emitted from the second transducer segment comprises:
a. determining a first positional offset prior to initial operation of the controllable actuator to move the first transducer segment relative to the second transducer segment; and
b. determining a second positional offset upon stoppage of the controllable actuator to track the motion of the first transducer segment and the second transducer segment.

4. The method of claim 3, further comprising the step of performing continuous determinations of positional offsets during operation of the controllable actuator to track the position of the first transducer segment relative to the second transducer segment.

5. The method of claim 3, wherein the controllable actuator is a controllable shape memory material.

\* \* \* \* \*